(12) United States Patent
Wu et al.

(10) Patent No.: US 10,196,523 B2
(45) Date of Patent: Feb. 5, 2019

(54) FUNCTIONALIZED QUINACRIDONE PIGMENTS

(71) Applicant: E Ink Corporation, Billerica, MA (US)

(72) Inventors: Ziyan Wu, Wayland, MA (US); Jason D. Feick, Auburndale, MA (US)

(73) Assignee: E Ink Corporation, Billerica, MA (US)

( * ) Notice: Subject to any disclaimer, the term of this patent is extended or adjusted under 35 U.S.C. 154(b) by 0 days.

(21) Appl. No.: 15/667,037

(22) Filed: Aug. 2, 2017

(65) Prior Publication Data

US 2017/0327692 A1 Nov. 16, 2017

Related U.S. Application Data

(62) Division of application No. 15/347,995, filed on Nov. 10, 2016, now Pat. No. 9,752,034.

(Continued)

(51) Int. Cl.
*C07D 471/04* (2006.01)
*C09D 11/52* (2014.01)
(Continued)

(52) U.S. Cl.
CPC .......... *C09B 69/109* (2013.01); *C07D 471/04* (2013.01); *C08F 120/18* (2013.01); *C09B 48/00* (2013.01); *C09D 4/00* (2013.01); *C09D 5/24* (2013.01); *C09D 5/4411* (2013.01); *C09D 11/033* (2013.01); *C09D 11/037* (2013.01); *C09D 11/107* (2013.01); *C09D 11/52* (2013.01); *G02F 1/167* (2013.01); *G02F 2001/1678* (2013.01)

(58) Field of Classification Search
CPC ..... C09B 69/109; C09B 48/00; C07D 471/04; C08F 120/18; C08F 220/18; C08F 2001/1678; G02F 1/167; C09D 4/00; C09D 11/52; C09D 11/033; C09D 11/037; C09D 11/107; C09D 5/4411; C09D 5/24
USPC ............................................. 8/454
See application file for complete search history.

(56) References Cited

U.S. PATENT DOCUMENTS 4,418,346 A  11/1983 Batchelder
5,122,611 A   6/1992 Tanaka
(Continued)

FOREIGN PATENT DOCUMENTS

JP  2011158783 A  8/2011
WO  2007060254 A2  5/2007

OTHER PUBLICATIONS

Yamaguchi, Y. et al., "Toner display using insulative particles charged triboelectrically", Asia Display/IDW '01, pp. 1729-1730, Paper AMD4-4 (2001).

(Continued)

*Primary Examiner* — William K Cheung
(74) *Attorney, Agent, or Firm* — Brian D. Bean

(57) ABSTRACT

Quinacridone pigments that are surface-functionalized with glycidyl methacrylate, maleic anhydride, or 4-methacryloxyethyl trimellitic anhydride to create a functionalized pigment. The functional groups are then activated to bond hydrophobic polymers, thereby coating the pigment with the hydrophobic polymers. The quinacridone pigments can be used for a variety of applications. They are well-suited for use in electro-optic materials, such as electrophoretic media for use in electrophoretic displays.

8 Claims, 3 Drawing Sheets

Related U.S. Application Data

(60) Provisional application No. 62/253,775, filed on Nov. 11, 2015.

(51) Int. Cl.

| | |
|---|---|
| *C09D 11/107* | (2014.01) |
| *C08F 120/18* | (2006.01) |
| *C09D 5/24* | (2006.01) |
| *G02F 1/167* | (2006.01) |
| *C09D 4/00* | (2006.01) |
| *C09D 11/033* | (2014.01) |
| *C09D 11/037* | (2014.01) |
| *C09B 48/00* | (2006.01) |
| *C09B 69/10* | (2006.01) |
| *C09D 5/44* | (2006.01) |

(56) References Cited

U.S. PATENT DOCUMENTS

| | | |
|---|---|---|
| 5,725,651 A | 3/1998 | Zambounis |
| 5,872,552 A | 2/1999 | Gordon, II |
| 5,930,026 A | 7/1999 | Jacobson |
| 6,017,584 A | 1/2000 | Albert |
| 6,090,516 A * | 7/2000 | Choe .................. C07C 69/82 430/108.22 |
| 6,130,774 A | 10/2000 | Albert |
| 6,144,361 A | 11/2000 | Gordon, II |
| 6,172,798 B1 | 1/2001 | Albert |
| 6,184,856 B1 | 2/2001 | Gordon, II |
| 6,225,971 B1 | 5/2001 | Gordon, II |
| 6,241,921 B1 | 6/2001 | Jacobson |
| 6,271,823 B1 | 8/2001 | Gordon, II |
| 6,445,489 B1 | 9/2002 | Jacobson |
| 6,504,524 B1 | 1/2003 | Gates |
| 6,512,354 B2 | 1/2003 | Jacobson |
| 6,531,997 B1 | 3/2003 | Gates |
| 6,664,944 B1 | 12/2003 | Albert |
| 6,672,921 B1 | 1/2004 | Liang |
| 6,693,620 B1 | 2/2004 | Herb |
| 6,727,873 B2 | 4/2004 | Gordon, II |
| 6,753,999 B2 | 6/2004 | Zehner |
| 6,788,449 B2 | 9/2004 | Liang |
| 6,822,782 B2 | 11/2004 | Honeyman |
| 6,825,970 B2 | 11/2004 | Goenaga |
| 6,864,875 B2 | 3/2005 | Drzaic |
| 6,866,760 B2 | 3/2005 | Paolini, Jr. |
| 6,900,851 B2 | 5/2005 | Morrison |
| 6,922,276 B2 | 7/2005 | Zhang et al. |
| 6,950,220 B2 | 9/2005 | Abramson et al. |
| 6,982,178 B2 | 1/2006 | LeCain et al. |
| 6,995,550 B2 | 2/2006 | Jacobson |
| 7,002,728 B2 | 2/2006 | Pullen et al. |
| 7,012,600 B2 | 3/2006 | Zehner |
| 7,012,735 B2 | 3/2006 | Honeyman et al. |
| 7,023,420 B2 | 4/2006 | Comiskey et al. |
| 7,034,783 B2 | 4/2006 | Gates |
| 7,038,655 B2 | 5/2006 | Herb |
| 7,075,502 B1 | 7/2006 | Drzaic |
| 7,116,318 B2 | 10/2006 | Amundson et al. |
| 7,116,466 B2 | 10/2006 | Whitesides et al. |
| 7,119,772 B2 | 10/2006 | Amundson |
| 7,167,155 B1 | 1/2007 | Albert et al. |
| 7,170,670 B2 | 1/2007 | Webber |
| 7,193,625 B2 | 3/2007 | Danner et al. |
| 7,202,847 B2 | 4/2007 | Gates |
| 7,236,291 B2 | 6/2007 | Kaga |
| 7,259,744 B2 | 8/2007 | Arango |
| 7,304,787 B2 | 12/2007 | Whitesides et al. |
| 7,312,784 B2 | 12/2007 | Baucom et al. |
| 7,312,794 B2 | 12/2007 | Zehner |
| 7,321,459 B2 | 1/2008 | Masuda et al. |
| 7,327,511 B2 | 2/2008 | Whitesides et al. |
| 7,339,715 B2 | 3/2008 | Webber et al. |
| 7,411,719 B2 | 8/2008 | Paolini, Jr. et al. |
| 7,420,549 B2 | 9/2008 | Jacobson |
| 7,453,445 B2 | 11/2008 | Amundson |
| 7,492,339 B2 | 2/2009 | Amundson |
| 7,528,822 B2 | 5/2009 | Amundson |
| 7,535,624 B2 | 5/2009 | Amundson et al. |
| 7,545,358 B2 | 6/2009 | Gates et al. |
| 7,561,324 B2 | 7/2009 | Duthaler et al. |
| 7,583,251 B2 | 9/2009 | Arango |
| 7,602,374 B2 | 10/2009 | Zehner |
| 7,612,760 B2 | 11/2009 | Kawai |
| 7,667,684 B2 | 2/2010 | Jacobson et al. |
| 7,679,599 B2 | 3/2010 | Kawai |
| 7,679,814 B2 | 3/2010 | Paolini, Jr. et al. |
| 7,688,297 B2 | 3/2010 | Zehner |
| 7,729,039 B2 | 6/2010 | LeCain et al. |
| 7,733,311 B2 | 6/2010 | Amundson |
| 7,733,335 B2 | 6/2010 | Zehner |
| 7,787,169 B2 | 8/2010 | Abramson et al. |
| 7,791,789 B2 | 9/2010 | Albert |
| 7,839,564 B2 | 11/2010 | Whitesides et al. |
| 7,846,992 B2 | 12/2010 | Deroover et al. |
| 7,910,175 B2 | 3/2011 | Webber |
| 7,952,557 B2 | 5/2011 | Amundson |
| 7,952,790 B2 | 5/2011 | Honeyman |
| 7,956,841 B2 | 6/2011 | Albert |
| 7,999,787 B2 | 8/2011 | Amundson |
| 8,009,348 B2 | 8/2011 | Zehner |
| 8,031,392 B2 | 10/2011 | Hiji |
| 8,040,594 B2 | 10/2011 | Paolini, Jr. |
| 8,054,526 B2 | 11/2011 | Bouchard |
| 8,068,090 B2 | 11/2011 | Machida |
| 8,077,141 B2 | 12/2011 | Duthaler |
| 8,098,418 B2 | 1/2012 | Paolini, Jr. |
| 8,102,363 B2 | 1/2012 | Hirayama |
| 8,125,501 B2 | 2/2012 | Amundson |
| 8,139,050 B2 | 3/2012 | Jacobson et al. |
| 8,174,490 B2 | 5/2012 | Whitesides |
| 8,197,584 B2 | 6/2012 | Claes et al. |
| 8,213,076 B2 | 7/2012 | Albert |
| 8,270,064 B2 | 9/2012 | Feick |
| 8,289,250 B2 | 10/2012 | Zehner |
| 8,300,006 B2 | 10/2012 | Zhou |
| 8,305,341 B2 | 11/2012 | Arango |
| 8,314,784 B2 | 11/2012 | Ohkami |
| 8,319,759 B2 | 11/2012 | Jacobson |
| 8,363,299 B2 | 1/2013 | Paolini, Jr. |
| 8,384,658 B2 | 2/2013 | Albert |
| 8,441,714 B2 | 5/2013 | Paolini, Jr. |
| 8,441,716 B2 | 5/2013 | Paolini, Jr. |
| 8,466,852 B2 | 6/2013 | Drzaic |
| 8,514,481 B2 | 8/2013 | Yeo |
| 8,558,783 B2 | 10/2013 | Wilcox |
| 8,558,785 B2 | 10/2013 | Zehner |
| 8,576,470 B2 | 11/2013 | Paolini, Jr. |
| 8,576,476 B2 | 11/2013 | Telfer |
| 8,582,196 B2 | 11/2013 | Walls |
| 8,593,396 B2 | 11/2013 | Amundson |
| 8,593,721 B2 | 11/2013 | Albert |
| 8,717,664 B2 | 5/2014 | Wang |
| 8,727,522 B2 | 5/2014 | Maekawa et al. |
| 8,791,896 B2 | 7/2014 | Kwon |
| 8,797,634 B2 | 8/2014 | Paolini, Jr. |
| 8,830,559 B2 | 9/2014 | Honeyman et al. |
| 8,873,129 B2 | 10/2014 | Paolini, Jr. |
| 8,896,519 B2 | 11/2014 | Hong et al. |
| 8,902,153 B2 | 12/2014 | Bouchard |
| 8,928,562 B2 | 1/2015 | Gates et al. |
| 8,969,886 B2 | 3/2015 | Amundson |
| 9,156,989 B2 | 10/2015 | Loccufier et al. |
| 9,170,467 B2 | 10/2015 | Whitesides |
| 9,199,441 B2 | 12/2015 | Danner |
| 9,230,492 B2 | 1/2016 | Harrington |
| 9,251,736 B2 | 2/2016 | Lin |
| 9,293,511 B2 | 3/2016 | Jacobson |
| 9,412,314 B2 | 8/2016 | Amundson |
| 9,541,814 B2 | 1/2017 | Lin |
| 9,688,859 B2 | 6/2017 | Yezek |
| 2003/0102858 A1 | 6/2003 | Jacobson |
| 2005/0124751 A1 | 6/2005 | Klingenberg et al. |

(56) References Cited

U.S. PATENT DOCUMENTS

| | | |
|---|---|---|
| 2005/0174341 A1 | 8/2005 | Johnson |
| 2005/0253777 A1 | 11/2005 | Zehner |
| 2007/0091418 A1 | 4/2007 | Danner et al. |
| 2007/0103427 A1 | 5/2007 | Zhou et al. |
| 2008/0024429 A1 | 1/2008 | Zehner |
| 2008/0024482 A1 | 1/2008 | Gates |
| 2008/0043318 A1 | 2/2008 | Whitesides |
| 2008/0048970 A1 | 2/2008 | Drzaic |
| 2008/0136774 A1 | 6/2008 | Harris |
| 2008/0291129 A1 | 11/2008 | Harris |
| 2009/0066685 A1 | 3/2009 | Gillies et al. |
| 2009/0174651 A1 | 7/2009 | Jacobson |
| 2009/0195568 A1 | 8/2009 | Sjodin |
| 2009/0225398 A1 | 9/2009 | Duthaler |
| 2009/0322721 A1 | 12/2009 | Zehner |
| 2010/0060628 A1 | 3/2010 | Lenssen et al. |
| 2010/0156780 A1 | 6/2010 | Jacobson |
| 2010/0220121 A1 | 9/2010 | Zehner |
| 2010/0265561 A1 | 10/2010 | Gates et al. |
| 2011/0193840 A1 | 8/2011 | Amundson |
| 2011/0193841 A1 | 8/2011 | Amundson |
| 2011/0199671 A1 | 8/2011 | Amundson |
| 2012/0205599 A1 | 8/2012 | Matsumoto |
| 2012/0293858 A1 | 11/2012 | Telfer |
| 2012/0326957 A1 | 12/2012 | Drzaic |
| 2014/0340430 A1 | 11/2014 | Telfer |

OTHER PUBLICATIONS

Kitamura, T. et al., "Electrical toner movement for electronic paper-like display", Asia Display/IDW '01, pp. 1517-1520, Paper HCS1-1 (2001).

Heikenfeld, J. et al., "A critical review of the present and future prospects for electronic paper", SID, 19(2), pp. 129-156 (2011).

Moilanen, David E. et al., "Water dynamics in large and small reverse micelles: From two ensembles to collective behavior", J. Chem. Phys., 131, 14704 (2009).

Hiemenz, P.C. et al., "Principles of Colloid and Surface Chemistry", 3rd ed., Marcel Dekker, NY, pp. 56-57 (1997).

Huang, Y et al. "Synthesis and Structure-Activity Relationships of Naphthamides as Dopamine D3 Receptor Ligands", J. Med. Chem. 44, pp. 1815-1826 (2001).

Hye, K.G. et al., "Preparation of Red Dyes Derived from Quinacridone Pigment by Introducing Nsubstituent and Their Characteristics as a Colorant for LCD Color Filter", Molecular Crystals and Liquid Crystals, 563:1, pp. 36-42, (Aug. 2, 2012).

Panina, N. et al., "Crystal structure prediction of organic pigments: quinacridone as an example", Journal of Applied Crystallography, vol. 40, pp. 105-114, (2007).

Dou, C. et al., "Novel, urea-functionalized quinacridone derivatives: Ultrasound and thermo effects on supramolecular organogels." Chemistry—A European Journal, vol. 16, No. 35, pp. 10744-10751 (2001).

Korean Intellectual Property Office, PCT/US2016/061250, International Search Report and Written Opinion, dated Feb. 14, 2017.

Ueno, U. et al, "Surface modification of an organic pigment by grafting of polymers: Graft polymerization . . . " Journal of the Japan Society of Colour Material, vol. 69, No. 11, pp. 743-749 (1996).

European Patent Office, EP Appl. No. 16864970.5, Extended European Search Report, dated Oct. 9, 2018.

\* cited by examiner

FUNCTIONALIZED QUINACRIDONE PIGMENTS

PRIOR APPLICATIONS

This application is a divisional application of U.S. application Ser. No. 15/347,995, filed Nov. 10, 2016, now issued as U.S. Pat. No. 9,752,034, which claims priority to U.S. Provisional Patent Application No. 62/253,755, filed Nov. 11, 2015. All of the aforementioned applications are incorporated herein by reference in their entireties.

BACKGROUND OF INVENTION

This invention relates to colored electrophoretic displays, and more specifically to electrophoretic displays capable of rendering more than two colors using a single layer of electrophoretic material comprising a plurality of colored particles.

The term color as used herein includes black and white. White particles are often of the light scattering type.

The term gray state is used herein in its conventional meaning in the imaging art to refer to a state intermediate two extreme optical states of a pixel, and does not necessarily imply a black-white transition between these two extreme states. For example, several of the E Ink patents and published applications referred to below describe electrophoretic displays in which the extreme states are white and deep blue, so that an intermediate gray state would actually be pale blue. Indeed, as already mentioned, the change in optical state may not be a color change at all. The terms black and white may be used hereinafter to refer to the two extreme optical states of a display, and should be understood as normally including extreme optical states which are not strictly black and white, for example the aforementioned white and dark blue states.

The terms bistable and bistability are used herein in their conventional meaning in the art to refer to displays comprising display elements having first and second display states differing in at least one optical property, and such that after any given element has been driven, by means of an addressing pulse of finite duration, to assume either its first or second display state, after the addressing pulse has terminated, that state will persist for at least several times, for example at least four times, the minimum duration of the addressing pulse required to change the state of the display element. It is shown in U.S. Pat. No. 7,170,670 that some particle-based electrophoretic displays capable of gray scale are stable not only in their extreme black and white states but also in their intermediate gray states, and the same is true of some other types of electro-optic displays. This type of display is properly called multi-stable rather than bistable, although for convenience the term bistable may be used herein to cover both bistable and multi-stable displays.

The term impulse, when used to refer to driving an electrophoretic display, is used herein to refer to the integral of the applied voltage with respect to time during the period in which the display is driven.

A particle that absorbs, scatters, or reflects light, either in a broad band or at selected wavelengths, is referred to herein as a colored or pigment particle. Various materials other than pigments (in the strict sense of that term as meaning insoluble colored materials) that absorb or reflect light, such as dyes or photonic crystals, etc., may also be used in the electrophoretic media and displays of the present invention.

Particle-based electrophoretic displays have been the subject of intense research and development for a number of years. In such displays, a plurality of charged particles (sometimes referred to as pigment particles) move through a fluid under the influence of an electric field. Electrophoretic displays can have attributes of good brightness and contrast, wide viewing angles, state bistability, and low power consumption when compared with liquid crystal displays. Nevertheless, problems with the long-term image quality of these displays have prevented their widespread usage. For example, particles that make up electrophoretic displays tend to settle, resulting in inadequate service-life for these displays.

As noted above, electrophoretic media require the presence of a fluid. In most prior art electrophoretic media, this fluid is a liquid, but electrophoretic media can be produced using gaseous fluids; see, for example, Kitamura, T., et al., Electrical toner movement for electronic paper-like display, IDW Japan, 2001, Paper HCS1-1, and Yamaguchi, Y., et al., Toner display using insulative particles charged triboelectrically, IDW Japan, 2001, Paper AMD4-4). See also U.S. Pat. Nos. 7,321,459 and 7,236,291. Such gas-based electrophoretic media appear to be susceptible to the same types of problems due to particle settling as liquid-based electrophoretic media, when the media are used in an orientation which permits such settling, for example in a sign where the medium is disposed in a vertical plane. Indeed, particle settling appears to be a more serious problem in gas-based electrophoretic media than in liquid-based ones, since the lower viscosity of gaseous suspending fluids as compared with liquid ones allows more rapid settling of the electrophoretic particles.

Numerous patents and applications assigned to or in the names of the Massachusetts Institute of Technology (MIT) and E Ink Corporation describe various technologies used in encapsulated electrophoretic and other electro-optic media. Such encapsulated media comprise numerous small capsules, each of which itself comprises an internal phase containing electrophoretically-mobile particles in a fluid medium, and a capsule wall surrounding the internal phase. Typically, the capsules are themselves held within a polymeric binder to form a coherent layer positioned between two electrodes. The technologies described in these patents and applications include:

(a) Electrophoretic particles, fluids and fluid additives; see for example U.S. Pat. Nos. 7,002,728 and 7,679,814;
(b) Capsules, binders and encapsulation processes; see for example U.S. Pat. Nos. 6,922,276 and 7,411,719;
(c) Films and sub-assemblies containing electro-optic materials; see for example U.S. Pat. Nos. 6,982,178 and 7,839,564;
(d) Backplanes, adhesive layers and other auxiliary layers and methods used in displays; see for example U.S. Pat. Nos. 7,116,318 and 7,535,624;
(e) Color formation and color adjustment; see for example U.S. Pat. Nos. 6,017,584; 6,664,944; 6,864,875; 7,075,502; 7,167,155; 7,667,684; 7,791,789; 7,956,841; 8,040,594; 8,054,526; 8,098,418; 8,213,076; and 8,363,299; and U.S. Patent Applications Publication Nos. 2004/0263947; 2007/0109219; 2007/0223079; 2008/0023332; 2008/0043318; 2008/0048970; 2009/0004442; 2009/0225398; 2010/0103502; 2010/0156780; 2011/0164307; 2011/0195629; 2011/0310461; 2012/0008188; 2012/0019898; 2012/0075687; 2012/0081779; 2012/0134009; 2012/0182597; 2012/0212462; 2012/0157269; and 2012/0326957;
(f) Methods for driving displays; see for example U.S. Pat. Nos. 5,930,026; 6,445,489; 6,504,524; 6,512,354;

6,531,997; 6,753,999; 6,825,970; 6,900,851; 6,995,550; 7,012,600; 7,023,420; 7,034,783; 7,116,466; 7,119,772; 7,193,625; 7,202,847; 7,259,744; 7,304,787; 7,312,794; 7,327,511; 7,453,445; 7,492,339; 7,528,822; 7,545,358; 7,583,251; 7,602,374; 7,612,760; 7,679,599; 7,688,297; 7,729,039; 7,733,311; 7,733,335; 7,787,169; 7,952,557; 7,956,841; 7,999,787; 8,077,141; 8,125,501; 8,139,050; 8,174,490; 8,289,250; 8,300,006; and 8,314,784; and U.S. Patent Applications Publication Nos. 2003/0102858; 2005/0122284; 2005/0179642; 2005/0253777; 2007/0091418; 2007/0103427; 2008/0024429; 2008/0024482; 2008/0136774; 2008/0150888; 2008/0291129; 2009/0174651; 2009/0179923; 2009/0195568; 2009/0322721; 2010/0045592; 2010/0220121; 2010/0220122; 2010/0265561; 2011/0187684; 2011/0193840; 2011/0193841; 2011/0199671; and 2011/0285754 (these patents and applications may hereinafter be referred to as the MEDEOD (MEthods for Driving Electro-optic Displays) applications);

(g) Applications of displays; see for example U.S. Pat. Nos. 7,312,784 and 8,009,348; and (h) Non-electrophoretic displays, as described in U.S. Pat. Nos. 6,241,921; 6,950,220; 7,420,549 and 8,319,759; and U.S. Patent Application Publication No. 2012/0293858.

Many of the aforementioned patents and applications recognize that the walls surrounding the discrete microcapsules in an encapsulated electrophoretic medium could be replaced by a continuous phase, thus producing a so-called polymer-dispersed electrophoretic display, in which the electrophoretic medium comprises a plurality of discrete droplets of an electrophoretic fluid and a continuous phase of a polymeric material, and that the discrete droplets of electrophoretic fluid within such a polymer-dispersed electrophoretic display may be regarded as capsules or microcapsules even though no discrete capsule membrane is associated with each individual droplet; see for example, U.S. Pat. No. 6,866,760. Accordingly, for purposes of the present application, such polymer-dispersed electrophoretic media are regarded as sub-species of encapsulated electrophoretic media.

A related type of electrophoretic display is a so-called microcell electrophoretic display. In a microcell electrophoretic display, the charged particles and the fluid are not encapsulated within microcapsules but instead are retained within a plurality of cavities formed within a carrier medium, typically a polymeric film. See, for example, U.S. Pat. Nos. 6,672,921 and 6,788,449, both assigned to Sipix Imaging, Inc.

Although electrophoretic media are often opaque (since, for example, in many electrophoretic media, the particles substantially block transmission of visible light through the display) and operate in a reflective mode, many electrophoretic displays can be made to operate in a so-called shutter mode in which one display state is substantially opaque and one is light-transmissive. See, for example, U.S. Pat. Nos. 5,872,552; 6,130,774; 6,144,361; 6,172,798; 6,271,823; 6,225,971; and 6,184,856. Dielectrophoretic displays, which are similar to electrophoretic displays but rely upon variations in electric field strength, can operate in a similar mode; see U.S. Pat. No. 4,418,346. Other types of electro-optic displays may also be capable of operating in shutter mode. Electro-optic media operating in shutter mode can be used in multi-layer structures for full color displays; in such structures, at least one layer adjacent the viewing surface of the display operates in shutter mode to expose or conceal a second layer more distant from the viewing surface.

An encapsulated electrophoretic display typically does not suffer from the clustering and settling failure mode of traditional electrophoretic devices and provides further advantages, such as the ability to print or coat the display on a wide variety of flexible and rigid substrates. (Use of the word printing is intended to include all forms of printing and coating, including, but without limitation: pre-metered coatings such as patch die coating, slot or extrusion coating, slide or cascade coating, curtain coating; roll coating such as knife over roll coating, forward and reverse roll coating; gravure coating; dip coating; spray coating; meniscus coating; spin coating; brush coating; air knife coating; silk screen printing processes; electrostatic printing processes; thermal printing processes; ink jet printing processes; electrophoretic deposition (See U.S. Pat. No. 7,339,715); and other similar techniques.) Thus, the resulting display can be flexible. Further, because the display medium can be printed (using a variety of methods), the display itself can be made inexpensively.

The aforementioned U.S. Pat. No. 6,982,178 describes a method of assembling a solid electro-optic display (including an encapsulated electrophoretic display) which is well adapted for mass production. Essentially, this patent describes a so-called front plane laminate (FPL) which comprises, in order, a light-transmissive electrically-conductive layer; a layer of a solid electro-optic medium in electrical contact with the electrically-conductive layer; an adhesive layer; and a release sheet. Typically, the light-transmissive electrically-conductive layer will be carried on a light-transmissive substrate, which is preferably flexible, in the sense that the substrate can be manually wrapped around a drum (say) 10 inches (254 mm) in diameter without permanent deformation. The term light-transmissive is used in this patent and herein to mean that the layer thus designated transmits sufficient light to enable an observer, looking through that layer, to observe the change in display states of the electro-optic medium, which will normally be viewed through the electrically-conductive layer and adjacent substrate (if present); in cases where the electro-optic medium displays a change in reflectivity at non-visible wavelengths, the term light-transmissive should of course be interpreted to refer to transmission of the relevant non-visible wavelengths. The substrate will typically be a polymeric film, and will normally have a thickness in the range of about 1 to about 25 mil (25 to 634 µm), preferably about 2 to about 10 mil (51 to 254 µm). The electrically-conductive layer is conveniently a thin metal or metal oxide layer of, for example, aluminum or ITO, or may be a conductive polymer. Poly(ethylene terephthalate) (PET) films coated with aluminum or ITO are available commercially, for example as aluminized Mylar (Mylar is a Registered Trade Mark) from E.I. du Pont de Nemours & Company, Wilmington Del., and such commercial materials may be used with good results in the front plane laminate.

Assembly of an electro-optic display using such a front plane laminate may be effected by removing the release sheet from the front plane laminate and contacting the adhesive layer with the backplane under conditions effective to cause the adhesive layer to adhere to the backplane, thereby securing the adhesive layer, layer of electro-optic medium and electrically-conductive layer to the backplane. This process is well-adapted to mass production since the front plane laminate may be mass produced, typically using roll-to-roll coating techniques, and then cut into pieces of any size needed for use with specific backplanes.

U.S. Pat. No. 7,561,324 describes a so-called double release sheet which is essentially a simplified version of the front plane laminate of the aforementioned U.S. Pat. No. 6,982,178. One form of the double release sheet comprises a layer of a solid electro-optic medium sandwiched between two adhesive layers, one or both of the adhesive layers being covered by a release sheet. Another form of the double release sheet comprises a layer of a solid electro-optic medium sandwiched between two release sheets. Both forms of the double release film are intended for use in a process generally similar to the process for assembling an electro-optic display from a front plane laminate already described, but involving two separate laminations; typically, in a first lamination the double release sheet is laminated to a front electrode to form a front sub-assembly, and then in a second lamination the front sub-assembly is laminated to a backplane to form the final display, although the order of these two laminations could be reversed if desired.

U.S. Pat. No. 7,839,564 describes a so-called inverted front plane laminate, which is a variant of the front plane laminate described in the aforementioned U.S. Pat. No. 6,982,178. This inverted front plane laminate comprises, in order, at least one of a light-transmissive protective layer and a light-transmissive electrically-conductive layer; an adhesive layer; a layer of a solid electro-optic medium; and a release sheet. This inverted front plane laminate is used to form an electro-optic display having a layer of lamination adhesive between the electro-optic layer and the front electrode or front substrate; a second, typically thin layer of adhesive may or may not be present between the electro-optic layer and a backplane. Such electro-optic displays can combine good resolution with good low temperature performance.

As indicated above most simple prior art electrophoretic media essentially display only two colors. Such electrophoretic media either use a single type of electrophoretic particle having a first color in a colored fluid having a second, different color (in which case, the first color is displayed when the particles lie adjacent the viewing surface of the display and the second color is displayed when the particles are spaced from the viewing surface), or first and second types of electrophoretic particles having differing first and second colors in an uncolored fluid (in which case, the first color is displayed when the first type of particles lie adjacent the viewing surface of the display and the second color is displayed when the second type of particles lie adjacent the viewing surface). Typically the two colors are black and white. If a full color display is desired, a color filter array may be deposited over the viewing surface of the monochrome (black and white) display. Displays with color filter arrays rely on area sharing and color blending to create color stimuli. The available display area is shared between three or four primary colors such as red/green/blue (RGB) or red/green/blue/white (RGBW), and the filters can be arranged in one-dimensional (stripe) or two-dimensional (2×2) repeat patterns. Other choices of primary colors or more than three primaries are also known in the art. The three (in the case of RGB displays) or four (in the case of RGBW displays) sub-pixels are chosen small enough so that at the intended viewing distance they visually blend together to a single pixel with a uniform color stimulus ('color blending'). The inherent disadvantage of area sharing is that the colorants are always present, and colors can only be modulated by switching the corresponding pixels of the underlying monochrome display to white or black (switching the corresponding primary colors on or off). For example, in an ideal RGBW display, each of the red, green, blue and white primaries occupy one fourth of the display area (one sub-pixel out of four), with the white sub-pixel being as bright as the underlying monochrome display white, and each of the colored sub-pixels being no lighter than one third of the monochrome display white. The brightness of the white color shown by the display as a whole cannot be more than one half of the brightness of the white sub-pixel (white areas of the display are produced by displaying the one white sub-pixel out of each four, plus each colored sub-pixel in its colored form being equivalent to one third of a white sub-pixel, so the three colored sub-pixels combined contribute no more than the one white sub-pixel). The brightness and saturation of colors is lowered by area-sharing with color pixels switched to black. Area sharing is especially problematic when mixing yellow because it is lighter than any other color of equal brightness, and saturated yellow is almost as bright as white. Switching the blue pixels (one fourth of the display area) to black makes the yellow too dark.

Multilayer, stacked electrophoretic displays are known in the art; J. Heikenfeld, P. Drzaic, J-S Yeo and T. Koch, Journal of the SID, 19(2), 2011, pp. 129-156. In such displays, ambient light passes through images in each of the three subtractive primary colors, in precise analogy with conventional color printing. U.S. Pat. No. 6,727,873 describes a stacked electrophoretic display in which three layers of switchable cells are placed over a reflective background. Similar displays are known in which colored particles are moved laterally (see International Application No. WO 2008/065605) or, using a combination of vertical and lateral motion, sequestered into micropits. In both cases, each layer is provided with electrodes that serve to concentrate or disperse the colored particles on a pixel-by-pixel basis, so that each of the three layers requires a layer of thin-film transistors (TFT's) (two of the three layers of TFT's must be substantially transparent) and a light-transmissive counter-electrode. Such a complex arrangement of electrodes is costly to manufacture, and in the present state of the art it is difficult to provide an adequately transparent plane of pixel electrodes, especially as the white state of the display must be viewed through several layers of electrodes. Multi-layer displays also suffer from parallax problems as the thickness of the display stack approaches or exceeds the pixel size.

U.S. Applications Publication Nos. 2012/0008188 and 2012/0134009 describe multicolor electrophoretic displays having a single back plane comprising independently addressable pixel electrodes and a common, light-transmissive front electrode. Between the back plane and the front electrode is disposed a plurality of electrophoretic layers. Displays described in these applications are capable of rendering any of the primary colors (red, green, blue, cyan, magenta, yellow, white and black) at any pixel location. However, there are disadvantages to the use of multiple electrophoretic layers located between a single set of addressing electrodes. The electric field experienced by the particles in a particular layer is lower than would be the case for a single electrophoretic layer addressed with the same voltage. In addition, optical losses in an electrophoretic layer closest to the viewing surface (for example, caused by light scattering or unwanted absorption) may affect the appearance of images formed in underlying electrophoretic layers.

Attempts have been made to provide full-color electrophoretic displays using a single electrophoretic layer. See, for example, U.S. Patent Application Publication No. 2011/0134506. However, in the current state of the art such displays typically involve compromises such as slow switching speeds (as long as several seconds) or high addressing voltages.

The present invention provides polymer functionalized pigments suitable for use in full-color electrophoretic displays, among other applications.

SUMMARY OF INVENTION

The invention provides surface functionalized pigments and polymer coated pigments including the surface functionalization. The pigments of the invention are easily dispersed in non-polar and/or hydrophobic fluids, and may be useful for a variety of applications such as paints, printing, e.g., inkjet printing, color filter fabrication, and incorporation into electro-optic displays, e.g., electrophoretic displays, where they may be used as a part of the electrophoretic medium.

The invention includes colored pigments comprising Formula I:

FORMULA I

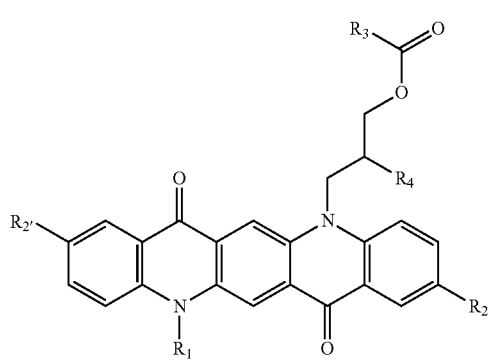

wherein $R_1$ is a hydrogen, $C_1$-$C_3$ alkyl group, or a halogen, or —$CH_2CHR_4CH_2OCOR_3$, $R_2$ is a hydrogen, $C_1$-$C_3$ alkyl group, or a halogen, $R_3$ is —$C(CH_3)CH_2$, or a hydrophobic polymer having a molecular weight between 5 kD and 100 kD; and $R_4$ is —OH or —O[$CH_2CH(CH_2OCOC(CH_3)CH_2$) O]$_x$H, and x is an integer from 1 to 15. Typically the pigment is magenta, red, violet, or pink, however multiple species of Formula I can be combined to tune a bulk pigment to the desired color. In one embodiment, the pigment of Formula I is reacted with a hydrophobic polymer, such as a polymer comprising a methacrylate or acrylate, such as lauryl acrylate, lauryl methacrylate, 2-ethylhexyl acrylate, 2-ethylhexyl methacrylate, hexyl acrylate, hexyl methacrylate, n-octyl acrylate, n-octyl methacrylate, n-octadecyl acrylate, or n-octadecyl methacrylate.

In some embodiment, the functionalized pigment is of Formula II:

FORMULA II wherein $R_2$, $R_4$, and x are as described above with respect to Formula I. In one embodiment, the pigment of Formula II is reacted with a hydrophobic polymer, such as a polymer comprising a methacrylate or acrylate, such as lauryl acrylate, lauryl methacrylate, 2-ethylhexyl acrylate, 2-ethylhexyl methacrylate, hexyl acrylate, hexyl methacrylate, n-octyl acrylate, n-octyl methacrylate, n-octadecyl acrylate, or n-octadecyl methacrylate.

In some embodiments, the polymer functionalized pigment is of Formula III:

Formula III wherein $R_1$ and $R_2$ are as described above with respect to Formula I, and m and n are independently integers between 10 and 200.

In some embodiments, the polymer functionalized pigment is of Formula IV:

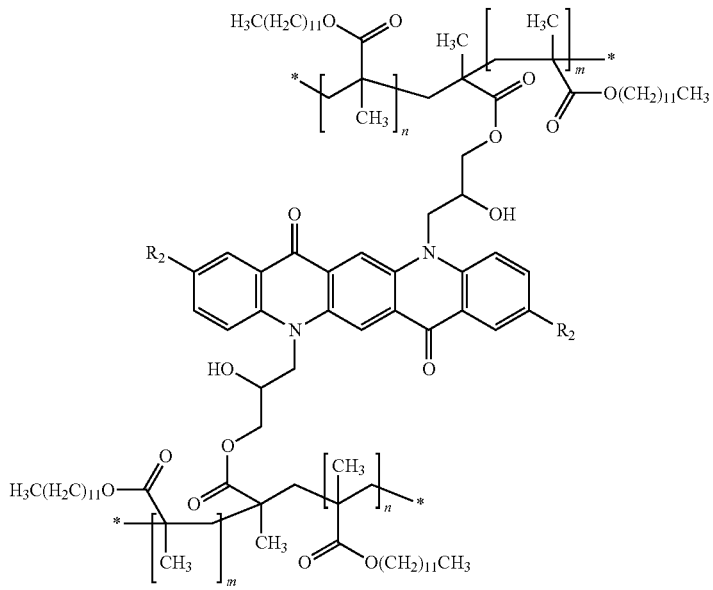

FORMULA IV wherein $R_2$ is as defined above with respect to Formula I, and m and n are independently integers between 10 and 200.

The hydrophobic polymer improves the dispersion of the pigment, especially when it is used in an electrophoretic medium. As a result, electrophoretic media including the pigments of the invention have a greater dynamic range between "white" and "colored" states. The pigments of the invention also switch between "white" and "colored" states faster than similarly-colored state-of-the-art pigments when both pigments are driven with the same voltage.

In other aspects, the invention includes colored pigments comprising Formula VI:

FORMULA VI wherein $R_1$ is a hydrogen, a $C_1$-$C_3$ alkyl group, a halogen, a hydroxyl, or —COCR$_3$CR$_4$COOH, $R_2$ is a hydrogen, $C_1$-$C_3$ alkyl group, or a halogen, $R_3$ is hydrogen or a hydrophobic polymer having a molecular weight between 5 kD and 100 kD, and is hydrogen or a hydrophobic polymer having a molecular weight between 5 kD and 100 kD. Typically the pigment is magenta, red, violet, or pink, however multiple species of Formula VI can be combined to tune a bulk pigment to the desired color. In one embodiment, the pigment of Formula VI is reacted with a hydrophobic polymer, such as a methacrylate or acrylate, such as lauryl acrylate, lauryl methacrylate, 2-ethylhexyl acrylate, 2-ethylhexyl methacrylate, hexyl acrylate, hexyl methacrylate, n-octyl acrylate, n-octyl methacrylate, n-octadecyl acrylate, or n-octadecyl methacrylate.

In some embodiment, the polymer functionalized pigment is of Formula VII:

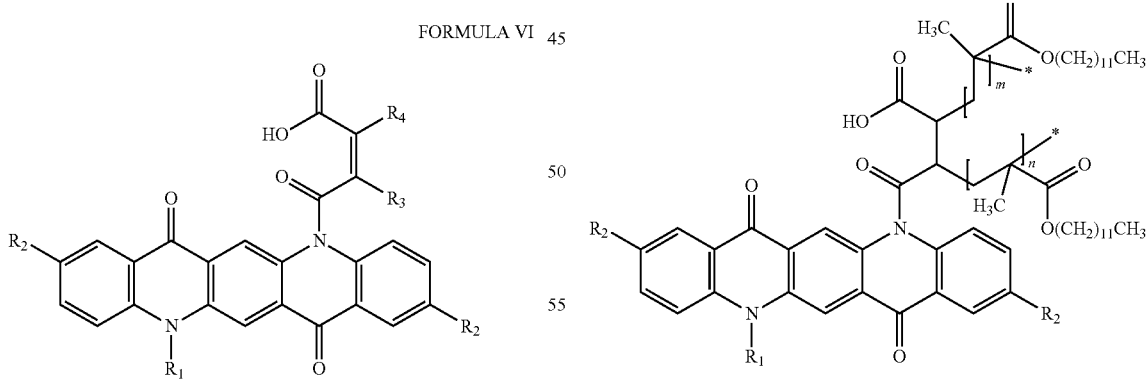

Formula VII wherein $R_1$ and $R_2$ are as defined above with respect to Formula VI, and m and n are independently integers between 10 and 200.

In some embodiment, the polymer functionalized pigment is of Formula VIII:

FORMULA VIII

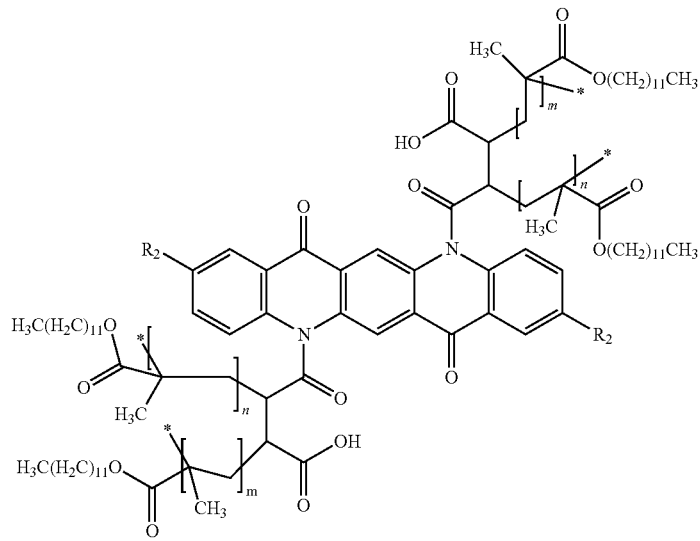

wherein $R_2$ is as defined above with respect to Formula VI, and m and n are independently integers between 10 and 200.

The hydrophobic polymer improves the dispersion of the pigment, especially when it is used in an electrophoretic medium. As a result, electrophoretic media including the pigments of the invention have a greater dynamic range between "white" and "colored" states. The pigments of the invention also switch between "white" and "colored" states faster than similarly-colored state-of-the-art pigments when both pigments are driven with the same voltage.

The invention additional includes methods of making functionalized pigments of Formula V:

FORMULA V

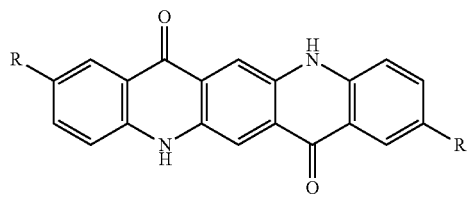

wherein R is a hydrogen, $C_1$-$C_3$ alkyl group, or a halogen. For example, pigments of Formulas I-IV, and VI-VIII (above) can be created using the methods of the invention. The method includes providing a pigment comprising a colored species of Formula V and reacting the pigment with glycidyl methacrylate, maleic anhydride, or 4-methacryloxyethyl trimellitic anhydride monomers to create a functionalized pigment. Functionalizing pigments of Formula V with glycidyl methacrylate, maleic anhydride, or 4-methacryloxyethyl trimellitic anhydride monomers can be achieved faster and with greater efficiency than prior art methods of functionalizing pigments of Formula V. Once the functionalized pigments have been prepared, the functionalized pigments can be combined with hydrophobic polymers, such as a methacrylate or acrylate, such as lauryl acrylate, lauryl methacrylate, 2-ethylhexyl acrylate, 2-ethylhexyl methacrylate, hexyl acrylate, hexyl methacrylate, n-octyl acrylate, n-octyl methacrylate, n-octadecyl acrylate, or n-octadecyl methacrylate. In some instances, the hydrophobic polymer is lauryl methacrylate. In some instances, the hydrophobic polymer and the functionalized pigment are ball milled prior to reacting.

The described pigments can be used in an electrophoretic medium comprising a fluid and first, second, and third species of particles disposed in the fluid. The first species of particles bear charges of one polarity, while the second and third species of particles bear charges of the opposite polarity. The characteristics of the first, second and third species of particles are such that the particle-particle interactions are less between the particles of the first species and the particles of the second species than between the particles of the first species and the particles of the third species. When a first addressing impulse is applied to the electrophoretic medium, the first and third species of particles move in one direction relative to the electric field and the second species of particles move in the opposed direction relative to the electric field. When a second addressing impulse, larger than the first addressing impulse but of the same polarity is applied to the electrophoretic medium, the first species of particles move in said one direction relative to the electric field, while the second and third species of particles move in said opposed direction relative to the electric field.

In another aspect, this invention provides an electrophoretic display capable of rendering multiple different colors, the display comprising an electrophoretic medium and first and second electrodes disposed on opposed sides of the electrophoretic medium. The electrophoretic medium comprises a fluid and a plurality of a first species of particles having a negative charge, a plurality a second species of particles having a positive charge, and a plurality of a third species of particles having a positive charge.

In another aspect, this invention provides an electrophoretic medium comprising a fluid and first, second and third species of particles disposed in the fluid. The fluid is dyed a first color. The first species of particles are light-scattering, and bear charges of one polarity, while the second and third species of particles are non-light scattering, are of second and third colors respectively different from the first color and from each other, and bear charges of the opposite polarity. The characteristics of the first, second and third species of particles are such that the particle-particle interactions are less between the particles of the first species and the particles of the second species than between the particles of the first species and the particles of the third species.

This invention also provides an electrophoretic display capable of rendering multiple different colors, the display comprising an electrophoretic medium and first and second electrodes disposed on opposed sides of the electrophoretic medium. The electrophoretic medium comprises a fluid dyed a first color; a plurality of a first species of light-scattering particles having a negative charge; a plurality of a second species of non-light scattering particles having a second color and a positive charge; and a plurality of a third species of non-light-scattering particles having a third color and a positive charge.

Finally, the present invention provides an electrophoretic medium comprising a fluid and at least one type of charged particle disposed in the fluid and capable of moving through the fluid when an electric field is applied to the medium, the medium further comprising a charge-control adjuvant capable of imparting a more positive charge to the charged particles, wherein the charge-control adjuvant is a metal salt of a carboxylic acid, wherein the metal is chosen from the group consisting of lithium, magnesium, calcium, strontium, rubidium, barium, zinc, copper, tin, titanium, manganese, iron, vanadium, and aluminum.

This invention extends to a front plane laminate, double release sheet, inverted front plane laminate or electrophoretic display comprising an electrophoretic medium of the present invention. The displays of the present invention may be used in any application in which prior art electro-optic displays have been used. Thus, for example, the present displays may be used in electronic book readers, portable computers, tablet computers, cellular telephones, smart cards, signs, watches, shelf labels and flash drives.

DETAILED DESCRIPTION

Figure 1:
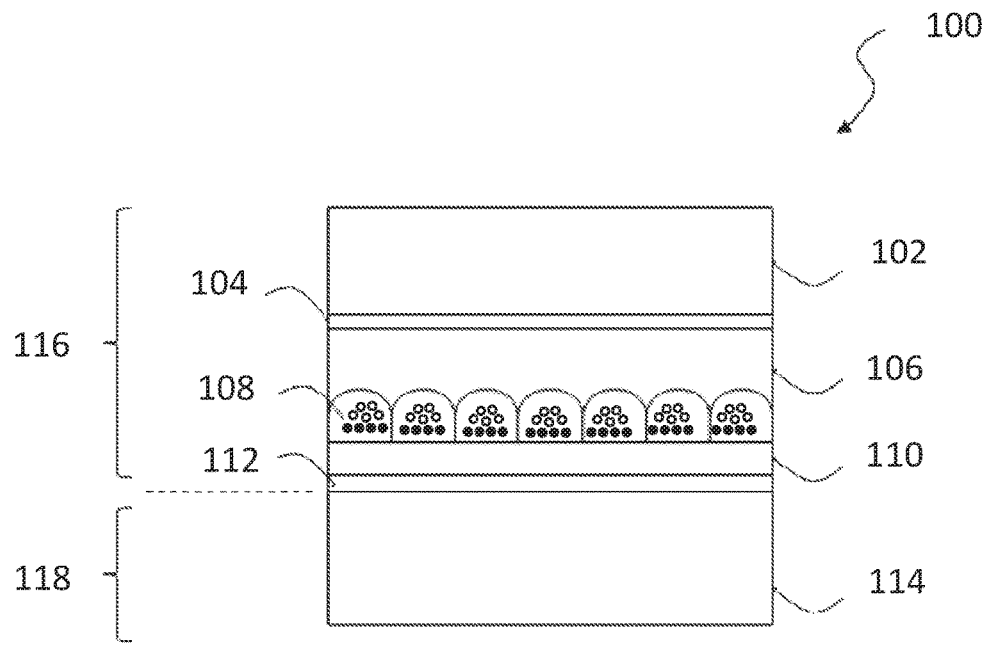
FIG. 1 of the accompanying drawings is a schematic cross-section through an exemplary electrophoretic display.

The invention includes improved pigments for use in paints, coatings, filters, and electrophoretic displays. In general, a quinacridone pigment can be surface functionalized with a functional molecule, such as glycidyl methacrylate, maleic anhydride, or 4-methacryloxyethyl trimellitic anhydride to create a functionalized pigment, whereupon the functional groups can be activated to bond hydrophobic polymers, thereby coating the pigment with the hydrophobic polymer. In some embodiments, the hydrophobic polymers will be methacrylates or acrylates, such as lauryl acrylate, lauryl methacrylate, 2-ethylhexyl acrylate, 2-ethylhexyl methacrylate, hexyl acrylate, hexyl methacrylate, n-octyl acrylate, n-octyl methacrylate, n-octadecyl acrylate, or n-octadecyl methacrylate. In some instances the quinacridone pigment will be functionalized with glycidyl methacrylate, and then polymer coated with lauryl methacrylate, resulting in polymer coated pigments of Formula IV, below:

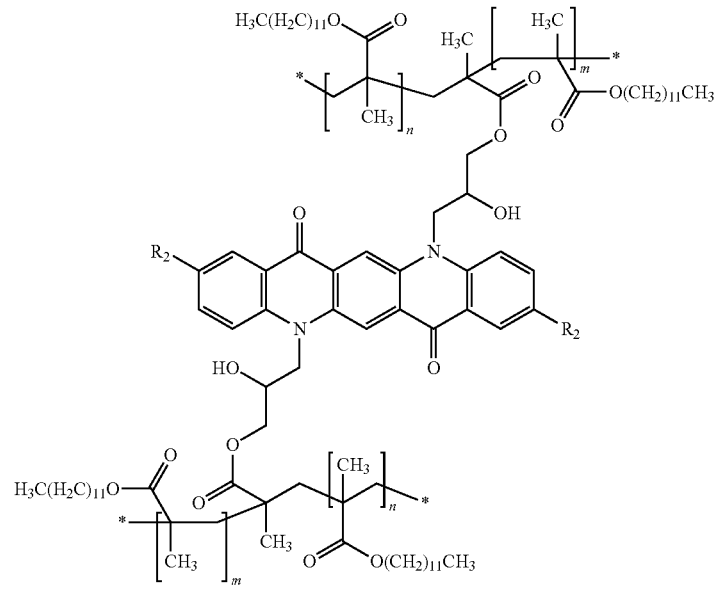

FORMULA IV wherein $R_2$ is a hydrogen, $C_1$-$C_3$ alkyl group, or a halogen, and m and n are independently positive integers between 10 and 200. In other embodiments, the quinacridone pigment will be functionalized with maleic anhydride, and then polymer coated with lauryl methacrylate, resulting in polymer coated pigments of Formula VIII, below:

FORMULA VIII

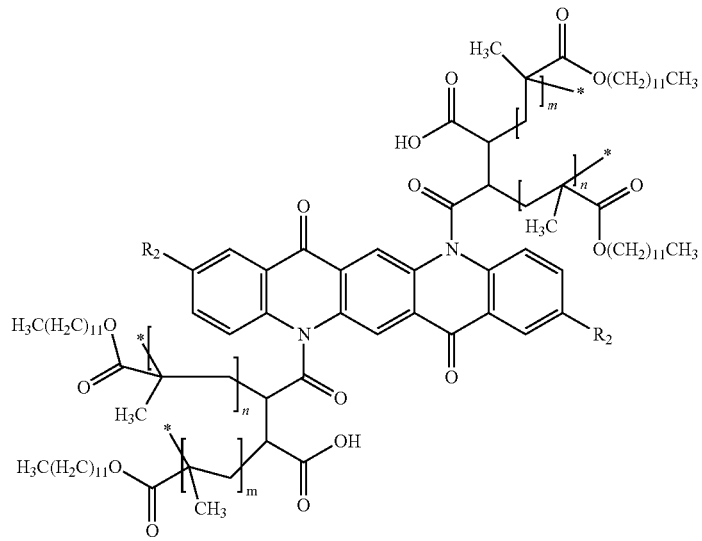

wherein $R_2$ is a hydrogen, $C_1$-$C_3$ alkyl group, or a halogen, and m and n are independently positive integers between 10 and 200.

In some embodiments, the pigments will be formed from functionalized pigments of Formula II:

FORMULA II

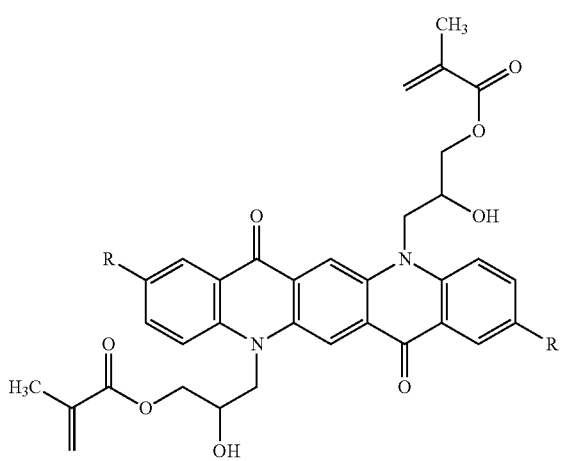

wherein $R_2$ is a hydrogen, $C_1$-$C_3$ alkyl group, or a halogen, $R_4$ is —OH or —O[$CH_2CH(CH_2OCOC(CH_3)CH_2)O]_xH$, and x is an integer from 1 to 15. For example, the pigments may be of Formula IX:

FORMULA IX

The functionalized pigments of any of the Formulae above can be coated with hydrophobic polymers, i.e., as described herein.

Functionalized pigment precursors, e.g., quinacridone pigments, e.g., quinacridone derivative pigments, typically exist as colored crystals prior to being functionalized. Accordingly the quinacridone molecules that are functionalized using the methods of the invention are often located at the outer surface of the crystal. Accordingly, a varying amount of functionalization may be achieved for individual quinacridone molecules depending upon the location and orientation of the quinacridone molecule with respect to the larger crystal structure. Additionally, during the functionalization and processing, it is likely that some amount of quinacridone will dissociate from the crystal, whereby the dissociated quinacridone may undergo complete functionalization and widespread coupling to the provided hydrophobic polymers. Details of quinacridone crystal structures can be found in the literature, for example Panina et al., *Journal of Applied Crystallography* (2007) p. 105-414, which is incorporated by reference in its entirety.

Displays of the present invention can reproduce the appearance of high quality color printing. Such high quality printing is typically effected using at least three colorants in a subtractive primary color system, typically cyan/magenta/yellow (CMY) and optionally black. It is often not appreciated that a so-called three-color CMY printing system is in reality a four-color system, the fourth color being the white background provided by the substrate (paper or similar) surface to which colorants are applied, and which performs the function of reflecting the light filtered by the subtractive colorants back to the viewer. Since there is no comparable background color in an essentially opaque electrophoretic medium unless it is being used in shutter mode, a non-shutter-mode electrophoretic medium should be capable of modulating four colors (white and three primary colors, the three primary colors typically being cyan, magenta and yellow, or red, green and blue). Optionally a black material may also be included, but it is possible to render black by a combination of cyan, magenta and yellow colors.

Before describing in detail preferred electrophoretic media and displays of the present invention, some general guidance will be given regarding materials for use in such media and displays, and preferred processes for their preparation.

The materials and processes used in preparing the media and displays of the present invention are generally similar to those used in similar prior art media and displays. As described for example in commonly-assigned U.S. Pat. No. 6,822,782, a typical electrophoretic medium comprises a fluid, a plurality of electrophoretic particles disposed in the fluid and capable of moving through the fluid (i.e., translating, and not simply rotating) upon application of an electric field to the fluid. The fluid also typically contains at least one charge control agent (CCA), a charging adjuvant, and a polymeric rheology modifier. These various components will now be described separately.

A: Fluid

The fluid contains the charged electrophoretic particles, which move through the fluid under the influence of an electric field. A preferred suspending fluid has a low dielectric constant (about 2), high volume resistivity (about $10^{15}$ Ohm·cm), low viscosity (less than 5 mPas), low toxicity and environmental impact, low water solubility (less than 10 parts per million (ppm), if traditional aqueous methods of encapsulation are to be used; note however that this requirement may be relaxed for non-encapsulated or certain microcell displays), a high boiling point (greater than about 90° C.), and a low refractive index (less than 1.5). The last requirement arises from the use of scattering (typically white) pigments of high refractive index, whose scattering efficiency depends upon a mismatch in refractive index between the particles and the fluid.

Organic solvents such as saturated linear or branched hydrocarbons, silicone oils, halogenated organic solvents, and low molecular weight halogen-containing polymers are some useful fluids. The fluid may comprise a single component or may be a blend of more than one component in order to tune its chemical and physical properties. Reactants or solvents for the microencapsulation process (if used), such as oil soluble monomers, can also be contained in the fluid.

Useful organic fluids include, but are not limited to, saturated or unsaturated hydrocarbons (such as, but are not limited to, dodecane, tetradecane, the aliphatic hydrocarbons in the ISOPAR® series (Exxon, Houston, Tex.), NORPAR® (Exxon, a series of normal paraffinic liquids), SHELL-SOL® (Shell, Houston, Tex.), and SOL-TROL® (Shell), naphtha, and other petroleum solvents; silicone oils (such as, but are not limited to, octamethyl cyclosiloxane and higher molecular weight cyclic siloxanes, poly(methyl phenyl siloxane), hexamethyldisiloxane, and polydimethylsiloxane; vinyl ethers, such as cyclohexyl vinyl ether and DECANT® (International Flavors & Fragrances, Inc., New York, N.Y.); aromatic hydrocarbons, such as toluene; and halogenated materials including, but not limited to, tetrafluorodibromoethylene, tetrachloroethylene, trifluorochloroethylene, 1,2, 4-trichlorobenzene and carbon tetrachloride and perfluoro- or partially-fluorinated hydrocarbons.

It is advantageous in some electrophoretic media of the present invention for the fluid to contain an optically absorbing dye. This dye must be soluble or dispersible in the fluid, but will generally be insoluble in the other components of the microcapsule. There is much flexibility in the choice of dye material. The dye can be a pure compound, or blends of dyes may be used to achieve a particular color, including black. The dyes can be fluorescent, which would produce a display in which the fluorescence properties depend on the position of the particles. The dyes can be photoactive, changing to another color or becoming colorless upon irradiation with either visible or ultraviolet light, providing another means for obtaining an optical response. Dyes could also be polymerizable by, for example, thermal, photochemical or chemical diffusion processes, forming a solid absorbing polymer inside the bounding shell.

Many dyes can be used in electrophoretic media. Important dye properties include light fastness, solubility or dispersibility in the fluid, color, and cost. The dyes are generally chosen from the classes of azo, azomethine, fluoran, anthraquinone, and triphenylmethane dyes and may be chemically modified so as to increase their solubility in the fluid and reduce their adsorption to the particle surfaces.

B: Electrophoretic Particles

The electrophoretic particles used in the media and displays of the present invention are preferably white, black, yellow, magenta, cyan, red, green, or blue in color, although other (spot) colors may also be used. There is much flexibility in the choice of such particles. For purposes of this invention, an electrophoretic particle is any particle that is insoluble in the fluid and charged or capable of acquiring a charge (i.e., has or is capable of acquiring electrophoretic mobility). In some cases, this mobility may be zero or close to zero (i.e., the particles will not move). The particles may be, for example, non-derivatized pigments or dyed (laked) pigments, or any other component that is charged or capable of acquiring a charge. Typical considerations for the electrophoretic particle are its optical properties, electrical properties, and surface chemistry. The particles may be organic or inorganic compounds, and they may either absorb light or scatter light, i.e., the particles for use in the invention may include scattering pigments, absorbing pigments and luminescent particles. The particles may be retroreflective or they may be electroluminescent, such as zinc sulfide particles, or they may be photoluminescent.

The electrophoretic particle may have any shape, i.e., spherical, plate-like or acicular. A scattering particle typically has high refractive index, high scattering coefficient, and low absorption coefficient and may be composed of an inorganic material such as rutile (titania), anatase (titania), barium sulfate, zirconium oxide, kaolin, or zinc oxide. Other particles are absorptive, such as carbon black or colored organic or inorganic pigments such as are used in paints and inks. A reflective material can also be employed, such as a metallic particle. Useful particle diameters may range from 10 nm up to about 10 μm, although for light-scattering particles it is preferred that the particle diameter not be smaller than about 200 nm.

Particularly preferred raw pigment particles of the present invention are red pigments such as Pigment Red 112, Pigment Red 179, Pigment Red 188 and Pigment Red 254 and magenta pigments such as Pigment Violet 19, Pigment Red 52:2 and Pigment Red 122. These pigments are based upon the quinacridone molecule, a version of which is shown below in Formula V:

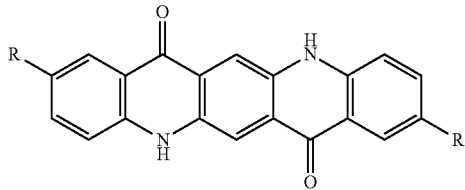

FORMULA V wherein R is a hydrogen, $C_1$-$C_3$ alkyl group, or a halogen. Other quinacridones, having structures not covered by Formula V, may also be polymer coated using the techniques described herein. A pre-milled combination of Pigment Violet 19 (CAS#1047-16-1) and Pigment Red 122 (CAS#980-26-7) is commercially available from Clariant (Basel, Switzerland) as Ink Jet Magenta E 02 VP2621.

The surface treatments described herein may also be used to surface-coat other pigments where the chemistry of the pigment is conducive to the methods described herein. Raw pigments for use in the electrophoretic particles include, but are not limited to, $PbCrO_4$, Cyan blue GT 55-3295 (American Cyanamid Company, Wayne, N.J.), Cibacron Black BG (Ciba Company, Inc., Newport, Del.), Cibacron Turquoise Blue G (Ciba), Cibalon Black BGL (Ciba), Orasol Black BRG (Ciba), Orasol Black RBL (Ciba), Acetamine Black, CBS (E. I. du Pont de Nemours and Company, Inc., Wilmington, Del., hereinafter abbreviated du Pont), Crocein Scarlet N Ex (du Pont) (27290), Fiber Black VF (du Pont) (30235), Luxol Fast Black L (du Pont) (Solv. Black 17), Nirosine Base No. 424 (du Pont) (50415 B), Oil Black BG (du Pont) (Solve Black 16), Rotalin Black RM (du Pont), Sevron Brilliant Red 3 B (du Pont); Basic Black DSC (Dye Specialties, Inc.), Hectolene Black (Dye Specialties, Inc.), Azosol Brilliant Blue B (GAF, Dyestuff and Chemical Division, Wayne, N.J.) (Solv. Blue 9), Azosol Brilliant Green BA (GAF) (Solv. Green 2), Azosol Fast Brilliant Red B (GAF), Azosol Fast Orange RA Conc. (GAF) (Solv. Orange 20), Azosol Fast Yellow GRA Conc. (GAF) (13900 A), Basic Black KMPA (GAF), Benzofix Black CW-CF (GAF) (35435), Cellitazol BNFV Ex Soluble CF (GAF) (Disp. Black 9), Celliton Fast Blue AF Ex Conc (GAF) (Disp. Blue 9), Cyper Black IA (GAF) (Basic Black 3), Diamine Black CAP Ex Cone (GAF) (30235), Diamond Black EAN Hi Con. CF (GAF) (15710), Diamond Black PBBA Ex (GAF) (16505); Direct Deep Black EA Ex CF (GAF) (30235), Hansa Yellow G (GAF) (11680); Indanthrene Black BBK Powd. (GAF) (59850), Indocarbon CLGS Conc. CF (GAF) (53295), Katigen Deep Black NND Hi Conc. CF (GAF) (15711), Rapidogen Black 3 G (GAF) (Azoic Black 4); Sulphone Cyanine Black BA-CF (GAF) (26370), Zambezi Black VD Ex Conc. (GAF) (30015); Rubanox Red CP-1495 (The Sherwin-Williams Company, Cleveland, Ohio) (15630); Raven 11 (Columbian Carbon Company, Atlanta, Ga.), (carbon black aggregates with a particle size of about 25 μm), Statex B-12 (Columbian Carbon Co.) (a furnace black of 33 μm average particle size), Greens 223 and 425 (The Shepherd Color Company, Cincinnati, Ohio 45246); Blacks 1, 1G and 430 (Shepherd); Yellow 14 (Shepherd); Krolor Yellow KO-788-D (Dominion Colour Corporation, North York, Ontario; KROLOR is a Registered Trade Mark); Red Synthetic 930 and 944 (Alabama Pigments Co., Green Pond, Ala. 35074), Krolor Oranges KO-786-D and KO-906-D (Dominion Colour Corporation); Green GX (Bayer); Green 56 (Bayer); Light Blue ZR (Bayer); Fast Black 100 (Bayer); Bayferrox 130M (Bayer BAYFERROX is a Registered Trade Mark); Black 444 (Shepherd); Light Blue 100 (Bayer); Light Blue 46 (Bayer); Yellow 6000 (First Color Co., Ltd., 1236-1, Jungwang-dong, Siheung-city, Kyonggi-do, Korea 429-450), Blues 214 and 385 (Shepherd); Violet 92 (Shepherd); and chrome green.

The electrophoretic particles may also include laked, or dyed, pigments. Laked pigments are particles that have a dye precipitated on them or which are stained. Lakes are metal salts of readily soluble anionic dyes. These are dyes of azo, triphenylmethane or anthraquinone structure containing one or more sulphonic or carboxylic acid groupings. They are usually precipitated by a calcium, barium or aluminum salt onto a substrate. Typical examples are peacock blue lake (Cl Pigment Blue 24) and Persian orange (lake of Cl Acid Orange 7), Black M Toner (GAF) (a mixture of carbon black and black dye precipitated on a lake).

It is preferred that pigments in the three subtractive primary colors (yellow, magenta and cyan) have high extinction coefficients and sufficiently small particle size as to be substantially non scattering of incident light.

Additional pigment properties which may be relevant are particle size distribution and light-fastness. Composite particle (i.e., polymeric particles that incorporate smaller pigment particles or dyes) may be used in the present invention. Pigments may be surface-functionalized as described below or may be used without functionalization.

It has long been known that the physical properties and surface characteristics of electrophoretic panicles can be modified by adsorbing various materials on to the surfaces of the particles, or chemically bonding various materials to these surfaces; see U.S. Pat. No. 6,822,782, especially column 4, line 27 to column 5, line 32. This same U.S. patent demonstrates that there is an optimum amount of polymer which should be deposited (too large a proportion of polymer in the modified particle causes an undesirable reduction in the electrophoretic mobility of the panicle) and that the structure of the polymer used to form the coating on the particle is important.

C: Charge Control Agents

The electrophoretic media of the present invention will typically contain a charge control agent (CCA), and may contain a charge director. These electrophoretic media components typically comprise low molecular weight surfactants, polymeric agents, or blends of one or more components and serve to stabilize or otherwise modify the sign and/or magnitude of the charge on the electrophoretic particles. The CCA is typically a molecule comprising ionic or other polar groupings, hereinafter referred to as head groups. At least one of the positive or negative ionic head groups is preferably attached to a non-polar chain (typically a hydrocarbon chain) that is hereinafter referred to as a tail group. It is thought that the CCA forms reverse micelles in the internal phase and that it is a small population of charged reverse micelles that leads to electrical conductivity in the very non-polar fluids typically used as electrophoretic fluids.

Reverse micelles comprise a highly polar core (that typically contains water) that may vary in size from 1 nm to tens of nanometers (and may have spherical, cylindrical, or other geometry) surrounded by the non-polar tail groups of the CCA molecule. Reverse micelles have been extensively studied, especially in ternary mixtures such as oil/water/surfactant mixtures. An example is the iso-octane/water/AOT mixture described, for example, in Fayer et al., *J. Chem. Phys.*, 131, 14704 (2009). In electrophoretic media, three phases may typically be distinguished: a solid particle having a surface, a highly polar phase that is distributed in the form of extremely small droplets (reverse micelles), and a continuous phase that comprises the fluid. Both the charged particles and the charged reverse micelles may move through the fluid upon application of an electric field, and thus there are two parallel pathways for electrical conduction through the fluid (which typically has a vanishingly small electrical conductivity itself).

The polar core of the CCA is thought to affect the charge on surfaces by adsorption onto the surfaces. In an electrophoretic display, such adsorption may be onto the surfaces of the electrophoretic particles or the interior walls of a microcapsule (or other solid phase, such as the walls of a microcell) to form structures similar to reverse micelles, these structures hereinafter being referred to as hemi-micelles. When one ion of an ion pair is attached more strongly to the surface than the other (for example, by covalent bonding), ion exchange between hemi-micelles and unbound reverse micelles can lead to charge separation in which the more strongly bound ion remains associated with the particle and the less strongly bound ion becomes incorporated into the core of a free reverse micelle.

It is also possible that the ionic materials forming the head group of the CCA may induce ion-pair formation at the particle (or other) surface. Thus the CCA may perform two basic functions: charge-generation at the surface and charge-separation from the surface. The charge-generation may result from an acid-base or an ion-exchange reaction between some moiety present in the CCA molecule or otherwise incorporated into the reverse micelle core or fluid, and the particle surface. Thus, useful CCA materials are those which are capable of participating in such a reaction, or any other charging reaction as known in the art.

Non-limiting classes of charge control agents which are useful in the media of the present invention include organic sulfates or sulfonates, metal soaps, block or comb copolymers, organic amides, organic zwitterions, and organic phosphates and phosphonates. Useful organic sulfates and sulfonates include, but are not limited to, sodium bis(2-ethylhexyl) sulfosuccinate, calcium dodecylbenzenesulfonate, calcium petroleum sulfonate, neutral or basic barium dinonylnaphthalene sulfonate, neutral or basic calcium dinonylnaphthalene sulfonate, dodecylbenzenesulfonic acid sodium salt, and ammonium lauryl sulfate. Useful metal soaps include, but are not limited to, basic or neutral barium petronate, calcium petronate, cobalt, calcium, copper, manganese, magnesium, nickel, zinc, aluminum and iron salts of carboxylic acids such as naphthenic, octanoic, oleic, palmitic, stearic, and myristic acids and the like. Useful block or comb copolymers include, but are not limited to, AB diblock copolymers of (A) polymers of 2-(N,N-dimethylamino)ethyl methacrylate quaternized with methyl p-toluenesulfonate and (B) poly(2-ethylhexyl methacrylate), and comb graft copolymers with oil soluble tails of poly(12-hydroxystearic acid) and having a molecular weight of about 1800, pendant on an oil-soluble anchor group of poly(methyl methacrylate-methacrylic acid). Useful organic amides/amines include, but are not limited to, polyisobutylene succinimides such as OLOA 371 or 1200 (available from Chevron Oronite Company LLC, Houston, Tex.), or SOLSPERSE® 17000 (available from Lubrizol, Wickliffe, Ohio), and N-vinylpyrrolidone polymers. Useful organic zwitterions include, but are not limited to, lecithin. Useful organic phosphates and phosphonates include, but are not limited to, the sodium salts of phosphated mono- and di-glycerides with saturated and unsaturated acid substituents. Useful tail groups for CCA include polymers of olefins such as polyisobutylene) of molecular weight in the range of 200-10,000. The head groups may be sulfonic, phosphoric or carboxylic acids or amides, or alternatively amino groups such as primary, secondary, tertiary or quaternary ammonium groups.

Charge adjuvants used in the media of the present invention may bias the charge on electrophoretic particle surfaces, as described in more detail below. Such charge adjuvants may be Bronsted or Lewis acids or bases.

Particle dispersion stabilizers may be added to prevent particle flocculation or attachment to the capsule or other walls or surfaces. For the typical high resistivity liquids used as fluids in electrophoretic displays, non-aqueous surfactants may be used. These include, but are not limited to, glycol ethers, acetylenic glycols, alkanolamides, sorbitol derivatives, alkyl amines, quaternary amines, imidazolines, dialkyl oxides, and sulfosuccinates.

D: Polymeric Additives

As described in U.S. Pat. No. 7,170,670, the bistability of electrophoretic media can be improved by including in the fluid a polymer having a number average molecular weight in excess of about 20,000, this polymer being essentially non-absorbing on the electrophoretic particles; polyisobutylene) is a preferred polymer for this purpose.

Also, as described in for example, U.S. Pat. No. 6,693,620, a particle with immobilized charge on its surface sets up an electrical double layer of opposite charge in a surrounding fluid. Ionic head groups of the CCA may be ion-paired with charged groups on the electrophoretic particle surface, forming a layer of immobilized or partially immobilized charged species. Outside this layer is a diffuse layer comprising charged (reverse) micelles comprising CCA molecules in the fluid. In conventional DC electrophoresis an applied electric field exerts a force on the fixed surface charges and an opposite force on the mobile counter-charges, such that slippage occurs within the diffuse layer and the particle moves relative to the fluid. The electric potential at the slip plane is known as the zeta potential.

FIG. 1 of the accompanying drawings is a schematic cross-section through an electrophoretic display (generally designated 100) of the present invention comprising an encapsulated electrophoretic medium; such a display, and methods for its manufacture are described in U.S. Pat. No. 6,982,178. The display 100 comprises a light-transmissive substrate 102, typically a transparent plastic film, such as a sheet of polyethylene terephthalate) (PET) about 25 to 200 µm in thickness. Although not shown in FIG. 1, the substrate 102 (the upper surface of which, as illustrated in FIG. 1, forms the viewing surface of the display) may comprise one or more additional layers, for example a protective layer to absorb ultra-violet radiation, barrier layers to prevent ingress of oxygen or moisture into the display, and anti-reflection coatings to improve the optical properties of the display.

The substrate 102 carries a thin, light-transmissive, electrically-conductive layer 104 that acts as the front electrode of the display. Layer 104 may comprise a continuous coating of electrically-conductive material with minimal intrinsic absorption of electromagnetic radiation in the visible spectral range such as indium tin oxide (ITO), poly(3,4-ethylenedioxythiophene) poly(styrenesulfonate) (PEDOT:PSS), graphene and the like, or may be a discontinuous layer of a material such as silver (in the form of, for example, nanowires or printed grids) or carbon (for example in nanotube form) that absorb or reflect visible light but are present at such a surface coverage that the layer as a whole is effectively transparent.

A layer (generically designated 108) of an electrophoretic medium is in electrical contact with the conductive layer 104 through an optional polymeric layer or layers 106, as described in more detail below. The electrophoretic medium 108 is shown as an encapsulated electrophoretic medium comprising a plurality of microcapsules. The microcapsules may be retained within a polymeric binder. Upon application of an electrical field across the layer 108, negatively-charged particles therein move towards the positive electrode and positively-charged particles move towards the negative electrode, so that the layer 108 appears, to an observer viewing the display through the substrate 102, to change color.

Although the display 100 is illustrated as having an encapsulated electrophoretic layer 108, this is not an essential feature of the present invention. Layer 108 may be encapsulated or comprise sealed or unsealed micro-cells or micro-cups, or may be non-encapsulated. When the layer is non-encapsulated, the electrophoretic internal phase (the electrophoretic particles and fluid) may be located between two planar electrodes, at least one of which is light-transmissive. The spacing between the electrodes may be controlled by the use of spacers, which may have the form of ribs or beads. Alternatively, the spacing may be controlled by the use of microcapsules containing the internal phase; the internal phase may be located within and outside the capsules. It is not necessary that the internal phase inside and outside the microcapsules be identical, although in certain circumstances this may be preferred. For example, if capsules containing the same internal phase as that outside the capsules are used as spacers it may be that the presence of the spacers is less easily discernible by a viewer of the display (since the internal and external internal phases would switch to at least substantially the same color).

As described in U.S. Pat. Nos. 6,982,178 and 7,012,735, the display 100 further comprises a layer 110 of lamination adhesive covering the electrophoretic layer 108. The lamination adhesive makes possible the construction of an electro-optic display by combining two subassemblies, namely a backplane 118 that comprises an array of pixel electrodes 112 and an appropriate arrangement of conductors to connect the pixel electrodes to drive circuitry, and a front plane 116 that comprises the substrate 102 bearing the transparent electrode 104, the electrophoretic layer 108, the lamination adhesive 110 and optional additional components such as polymeric layer or layers 106. To form the final display, the front plane 116 is laminated to the backplane 118 by means of lamination adhesive 110. The lamination adhesive may be cured thermally or by actinic radiation (for example, by UV curing) or may be uncured.

Since the lamination adhesive 110 is in the electrical path from the backplane electrodes 112 to the front electrode 104, its electrical properties must be carefully tailored. As described in U.S. Pat. No. 7,012,735 the lamination adhesive may comprise, in addition to a polymeric material, an ionic dopant that may be an additive selected from a salt, a polyelectrolyte, a polymer electrolyte, a solid electrolyte, a conductive metal powder, a ferrofluid, a non-reactive solvent, a conductive organic compound, and combinations thereof. The volume resistivities of encapsulated electrophoretic media of the present invention are typically around $10^{10}$ Ohm·cm, and the resistivities of other electro-optic media are usually of the same order of magnitude. Accordingly, the volume resistivity of the lamination adhesive is normally around $10^8$ to $10^{12}$ Ohm·cm at the operating temperature of the display; which is typically around 20° C.

Polymeric layer 106 may be a lamination adhesive layer with similar properties to those of lamination adhesive layer 110 (see for example U.S. Pat. No. 7,839,564), except that, since polymeric layer 106 is adjacent to the non-pixelated, light-transmissive common electrode 104, its electrical conductivity may be higher than that of lamination adhesive layer 110, which is adjacent to the pixelated back plane electrodes 112 and cannot be so conductive as to lead to significant currents flowing from one backplane electrode to its neighbors when they are held at different potentials during switching of the display. When polymeric layer 106 is a lamination adhesive it may be used to affix electrophoretic layer 108 to front electrode 104 during manufacture of the front plane as described in detail in the aforementioned U.S. Pat. No. 6,982,178.

As mentioned above, the present invention provides an electrophoretic medium comprising a fluid and at least a first species of particles disposed in the fluid, the first species of particles being such that when a first electric field is applied to the medium for a first period, thereby applying a first addressing impulse to the medium, the first species of particles move in one direction relative to the electric field, but when a second electric field, having the same polarity as the first electric field, is applied to the medium for a second period, thereby applying a second addressing impulse larger than the first addressing impulse to the medium, the first species of particles move in the opposed direction relative to the electric field. For the purpose of providing a better understanding of the present invention, the following hypothesis as to how the pigment particles might move in a first direction with a first addressing impulse (i.e., behaving as though the particles bore a negative charge) and in a second direction with a second, higher addressing impulse (i.e., behaving as though the particles bore a positive charge) is provided, but the invention is in no way limited by this hypothesis.

Various embodiments of electrophoretic media and displays of the present invention, and their use to form colored images, will now be described in more detail. In these embodiments the following general switching mechanisms are utilized:

(A) Conventional electrophoretic motion, in which particles with associated charge (either surface-bound or adsorbed) move in an electric field;

(B) Conventional racing particles, wherein particles of higher zeta potential move faster than particles of lower zeta potential (as described, for example, in U.S. Pat. No. 8,441,714 and earlier patents cited therein)

(C) Coulombic aggregation between particles of opposite sign, such that the aggregate moves in an electric field according to its net charge in the absence of an electrochemical (or displacement) current, but wherein the aggregate is separated by modulation of charge on at least one of the particles by the electrochemical (or displacement) current;

(D) Reversal of the direction of motion of at least one species of particles as a result of electrochemical (or displacement) current.

The waveforms used to drive displays of the present invention may modulate the electrical impulse provided to the display using any one or more of at least four different methods:

(i) Pulse width modulation, in which the duration of a pulse of a particular voltage is changed;

(ii) Duty cycle modulation, in which a sequence of pulses is provided whose duty cycle is changed according to the impulse desired;

(iii) Voltage modulation, in which the voltage supplied is changed according to the impulse required; and (iv) A DC voltage offset applied to an AC waveform (which itself has net zero impulse)

Which of these methods is used depends upon the intended application and the exact form of display used. As noted above, herein the term impulse is used to denote the integral of the applied voltage with respect to time during the period in which a medium or display is addressed. Also as noted above, a certain electrochemical or displacement current is required for the change in direction of a (typically negatively-charged) species of particle or the disaggregation of Coulombic aggregates, and thus when a high impulse is to applied to a medium of display, the addressing voltage must be sufficient to provide such a current. Lower impulses may be provided by lower addressing voltages, or by reduction in the addressing time at the same higher voltage. As noted above, there is a polarization phase during which electrochemical currents are not at their maximum value, and during this polarization phase the particles move according to their native charge (i.e., the charge they bear before any addressing voltage is applied to the medium or display. Thus, low-impulse addressing at high voltage is ideally for a duration such as to polarize the electrophoretic medium but not lead to high steady-state current flow.

Figures 2A, 2B:
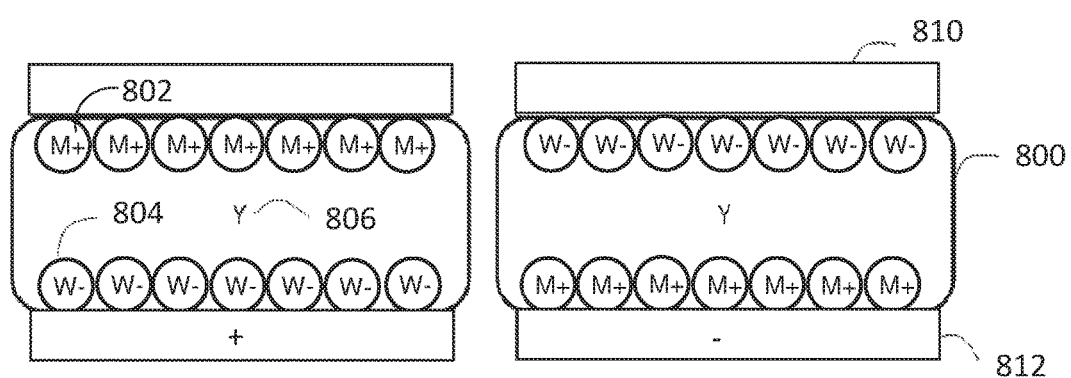
FIGS. 2A and 2B are schematic cross-sections through an encapsulated electrophoretic display including magenta particles showing two optical states of the display under first and second voltages.

FIGS. 2A and 2B are schematic cross-sections showing various possible states of single microcapsule 800 (a sealed or unsealed microcell, or other similar enclosure may alternatively be used), containing a fluid 806 dyed with a yellow dye (uncharged yellow particles may be substituted for the yellow dye. Disposed in the fluid 806 are positively-charged light-transmissive magenta particles 802 and negatively-charged white particles 804. On the upper side of microcapsule 800, as illustrated in FIGS. 2A and 2B, is a substantially transparent front electrode 810, the upper surface of which (as illustrated) forms the viewing surface of the display, while on the opposed side of the microcapsule 800 is a rear or pixel electrode 812. In FIGS. 2A and 2B, it will be assumed that the front electrode 810 remains at ground potential (although this is not an essential feature of the present invention, and variation of the potential of this electrode may be desirable in some instances, for example to provide higher electric fields), and that the electric field across microcapsule 800 is controlled by changing the voltage of the rear electrode 812.

FIGS. 2A and 2B illustrate separation of charged color particles (802 and 804) within the microcapsule 800 when a voltage is applied across an electrophoretic medium, thereby causing particles 802 and 804 to undergo electrophoretic motion. As shown in FIG. 2A, when the rear electrode 812 is at a positive voltage, the white particles 804 move towards the rear electrode 812, while the magenta particles 802 lie adjacent the front electrode 810. In this configuration, the microcapsule 800 displays a red color caused by the combination of the magenta particles and the yellow dye viewed against the white background provided by the white particles. (View is assumed to be above, but in the approximate plane of the figure in FIGS. 2A and 2B.) As shown in FIG. 2B, when the rear electrode 812 is at a negative voltage, the white particles 804 move adjacent the front electrode 810, and the microcapsule 800 displays a white color (both the yellow fluid 806 and the magenta particles 802 are masked by the white particles 804).

Obviously, other combinations of colored particles and dyes can be substituted for the white and magenta particles, and yellow dye, used in FIGS. 2A and 2B. Especially preferred embodiments of the present invention are those in which one dye or particle has one of the additive primary colors, and another is of the complementary subtractive primary color. Thus, for example, the dye might be cyan and the two particles white and red. Other combinations of particles, including multiple particle groups having the same charge polarity, but different charge magnitudes, are also possible. Additionally, green/magenta and blue/yellow combinations of dye and particle may be used, together with a white particle. The fluid 806 may optionally be colorless.

In one preferred embodiment of the present invention, the first (white) particle is a silanol-functionalized scattering material such as titanium dioxide to which a polymeric material has been attached; the second particle is a positively charged magenta material such as quinacridone pigment that has been coated as described below.

An electrophoretic display may additionally include a dye. The dye in some embodiments is a hydrocarbon (ISOPAR® E)-soluble material that may be an azo dye such as Sudan I or Sudan II or derivatives thereof. Other hydrocarbon-soluble dyes such as azomethine (yellow and cyan are readily available) or other materials that are well-known in the art may also be.

The following Examples are now given, though by way of illustration only, to shows details of particularly preferred materials, processes, conditions and techniques used to prepare the media and electrophoretic displays of the present invention.

Example 1—GMA Functionalized Pigments

This Example illustrates the preparation of a magenta polymer coated pigment and the incorporation of the pigment into a test display of the type illustrated in the accompanying drawings.

Part A: Preparation of a Magenta Pigment Dispersion

Ink Jet Magenta E 02 VP2621, available from Clariant, Basel, Switzerland, was dispersed in toluene. The resultant dispersion was transferred to a 500 mL round-bottomed flask and the flask degassed with nitrogen. The reaction mixture was then brought to 45° C., and, upon temperature equilibration, glycidyl methacrylate (GMA) monomer was added and the reaction was allowed to stir at 45° C. for four hours. The resulting reaction mixture was allowed to cool to room temperature and then poured into a 1 L plastic centrifuge bottle, diluted with toluene and centrifuged at 3500 RPM for 20 minutes. The centrifuge cake was washed twice with toluene, each time the mixture was centrifuged at 3500 RPM for 20 minutes. After the final wash, the supernatant was decanted and the resultant pigment was dried in a 70° C. vacuum oven overnight, then ground with a mortar and pestle. This procedure produces magenta pigment functionalized with an acrylate group to which a polymeric chain could be attached.

The dried functionalized pigment was then dispersed in toluene and lauryl methacrylate (LMA) monomer with ball milling with Zirconox grinding media and a roll mill, and the resultant dispersion transferred to a jacketed 500 mL rector equipped with an overhead stirrer and brought to 65° C. via a circulating water bath. The system was purged with nitrogen for at least one hour, and then a solution of AIBN (2,2'-azobis(2-methylpropionitrile)) in toluene was metered into the reaction. The reaction mixture was stirred vigorously at 65° C. for 16 hours, then poured into a 1 L plastic centrifuge bottle, diluted with toluene and centrifuged at 4500 RPM for 30 minutes. The centrifuge cake was washed once with toluene and the mixture was again centrifuged at 4500 RPM for 30 minutes. The supernatant was decanted and the resultant pigment was dried in a 70° C. vacuum oven overnight. This procedure produces a magenta pigment with a covalently bound polymeric shell with a typical molecular weight of 35-120 kDA. See Formula II. The polymerized pigment was then ground with a mortar and pestle, and dispersed in ISOPAR® E to form a 20 weight % dispersion, which was sonicated and rolled on a roll mill for 24 hours. The resultant dispersion was filtered through fabric mesh to remove any large particles, a sample removed and its solids content measured.

Part B: Preparation of Internal Phase

The magenta pigment dispersion prepared in Part A above (13.92 g of a 14% w/w dispersion in ISOPAR® E) was combined with 83.07 g of a 60% w/w ISOPAR® E dispersion of titanium dioxide (polymer coated as described in the aforementioned U.S. Pat. No. 7,002,728), 7.76 g of a 20% w/w solution of SOLSPERSE® 17000 in ISOPAR® E, a 15% w/w solution of polyisobutylene) of molecular weight 1270 kDa in ISOPAR® E (this polyisobutylene) acts as an image stabilizer; see U.S. Pat. No. 7,170,670), and 5.82 g of ISOPAR® E. The resultant mixture was dispersed overnight on a mechanical roller to produce an internal phase ready for encapsulation and having a conductivity of 304.7 pS/cm.

Part C: Microencapsulation

The internal phase prepared in Part B was encapsulated following the procedure described in U.S. Pat. No. 7,002,728. The resultant encapsulated material was isolated by sedimentation, washed with deionized water, and size-separated by sieving. Capsule size analysis using a Coulter Multisizer showed that the resulting capsules had a mean size of 40 μm and more than 85 percent of the total capsule volume was in capsules having the desired size of between 20 and 60 μm.

Part D: Preparation of Display

The sieved capsules produced in Part C above were adjusted to pH 9 with ammonium hydroxide solution and excess water removed. The capsules were then concentrated and the supernatant liquid discarded. The concentrated capsules were mixed with an aqueous polyurethane binder (prepared in a manner similar to that described in U.S. Patent Application Publication No. 2005/0124751) at a ratio of 1 part by weight binder to 15 parts by weight of capsules following which Triton X-100 surfactant and hydroxypropylmethylcellulose were added and mixed thoroughly to provide a slurry.

The capsule slurry thus prepared was coated onto the indium tin oxide (ITO) coated surface of a polyethylene terephthalate) (PET)/ITO film of 125 μm thickness using a bar coater, and the coated film dried at 60° C. Separately, a layer of polyurethane adhesive doped with tetraethylammonium hexafluorophosphate as a conductive dopant was coated onto a release sheet, and the resultant PET film/adhesive sub-assembly was laminated on top of the coated capsules as described in the above-mentioned U.S. Pat. No. 7,002,728. The release sheet was removed and the resultant multilayer structure was laminated onto a graphite rear electrode to produce an experimental single-pixel display comprising, in order from its viewing surface, the PET film, a layer of ITO, a capsule layer, a lamination adhesive layer, and the graphite rear electrode.

Part E: Electro-Optic Tests

The resulting displays were switched using a square-wave AC waveform applied to the graphite rear electrode (while the front ITO electrode was grounded) of ±30V and 50 Hz that was offset from zero as specified below. The DC offset for red/white switching was ±10V. In this case, the white and magenta pigments move though the non-polar fluid. The red state results from viewing of the magenta (green-absorbing) pigment against the white background. The DC offset for magenta/white switching was ±60V. The white color was obtained as the white pigment moved away from the viewing side of the display towards the negatively-charged rear electrode, as described above with reference to FIGS. 2A and 2B.

Magenta pigments functionalized with glycidyl methacrylate (GMA) and coated with lauryl methacrylate were compared to state-of-the art magenta pigments. The state-of-the-art pigments were produced as described in U.S. Patent Application No. 2014/0340430, which is incorporated by reference in its entirety. The state-of-the-art magenta pigments were produced in a manner similar to that described above in Part A, however the magenta pigment was functionalized with 4-vinylbenzylchloride (VBA) prior to coating with lauryl methacrylate (LMA). The amount of functionalized monomer and the amount of surface coating polymer were also varied to evaluate how these features altered the overall performance of the pigment in an electrophoretic display.

Figure 3:
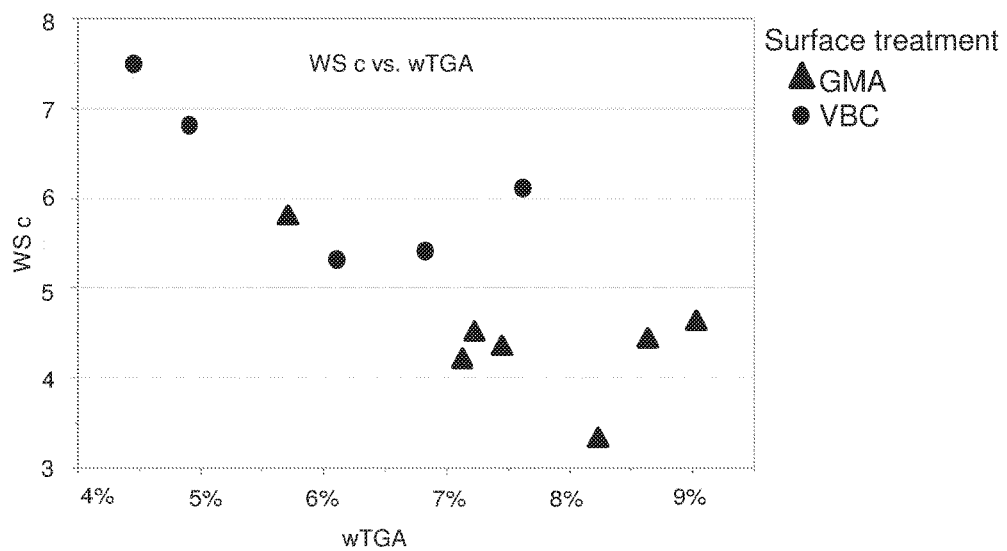
FIG. 3 shows white state contamination (WSc) as a function of washed thermogravimetric analysis (wTGA), where the wTGA values were modified by changing the level of functionalization and/or the amount of polymer coating.
Figure 4:
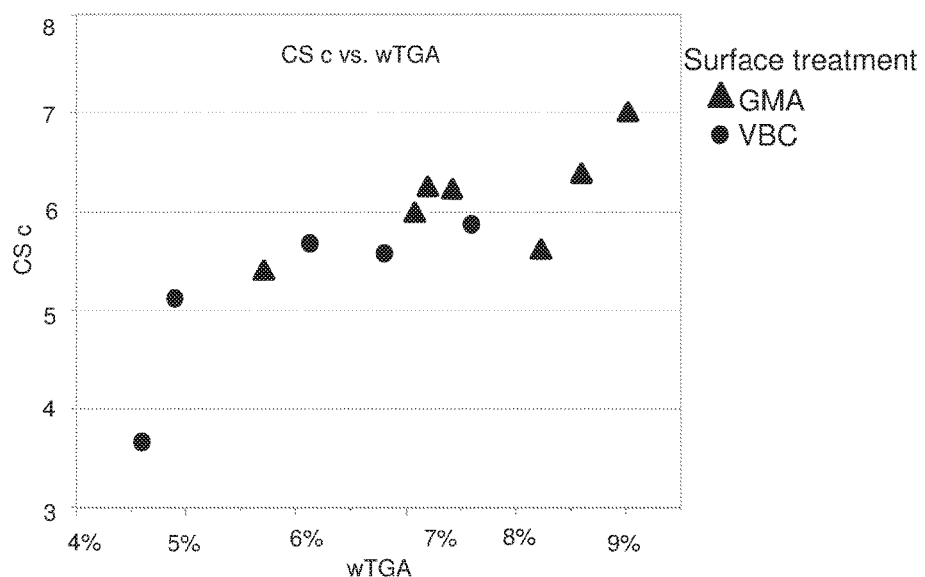
FIG. 4 shows color saturation (CSc) as a function of washed thermogravimetric analysis (wTGA), where the wTGA values were modified by changing the level of functionalization and/or the amount of polymer coating.

Experience with colored electrophoretic systems using hydrophobic fluids suggests that better switching and color states are achieved with pigments having high organics content, typically representing a pigment with a dense polymer shell around the pigment. The quality of the polymer coating can be evaluated with a number of analytical techniques and/or imaging. Nonetheless, it is very straightforward to evaluate pigments for organics content using thermogravimetric analysis (TGA), (FIGS. 3 and 4 refer to "washed" TGA because the pigments were washed in tetrahydrofuran to assure that any loose polymer was removed from the pigment.) As shown in FIGS. 3 and 4, the overall performance of a colored/white pigment system in an electrophoretic display roughly tracks TGA. This is not strictly the case, however; white state contamination (WS c) and color saturation (CS c) do vary somewhat for magenta pigments with the same polymer coating weight but different functional elements (GMA vs. VBC). Compare, for example, the points for GMA and VBC with a wTGA of about 7%, where the white state contamination of the GMA pigment particles is clearly better.

A series of functionalized and polymer coated pigments were prepared as shown in Table 1. The pigments were analyzed for organic content using thermogravimetric analysis, as discussed above.

TABLE 1

Thermogravimetric analysis of polymer coated pigments.

| Pigment | Experiment | Mw | Mn | PDI | Mz | Mp | TGA | Washed TGA | Free Polymer | ZP (mV) |
|---|---|---|---|---|---|---|---|---|---|---|
| 1040-50-EFGHIJK | VBC 10 L | 65827 | 33428 | 1.97 | 65079 | 108659 | 7.2% | 4.7% | 34.5% | |
| 1013-34-P4 | VBC_1.75 × LMA | 69374 | 29238 | 2.37 | 119671 | 72303 | 11.8% | 6.1% | 47.9% | 37.8 |
| 1013-26-P | 1 × GMA_1 × LMA | 78956 | 34834 | 2.27 | 143320 | 79894 | 11.0% | 8.1% | 26.9% | |
| 1013-27-P2 | 1 × GMA_1.25 × LMA | 76125 | 28661 | 2.66 | 173878 | 61459 | 12.8% | 9.2% | 28.2% | |
| 1013-34-P3 | 1 × GMA_1.75 × LMA | 79184 | 29128 | 2.72 | 149551 | 79030 | 14.8% | 10.3% | 30.3% | 40.0 |
| 1013-34-P2 | 2 × GMA_1.75 × LMA | 81256 | 30598 | 2.66 | 155098 | 79030 | 15.2% | 11.3% | 25.6% | 43.0 |

Figure 5:
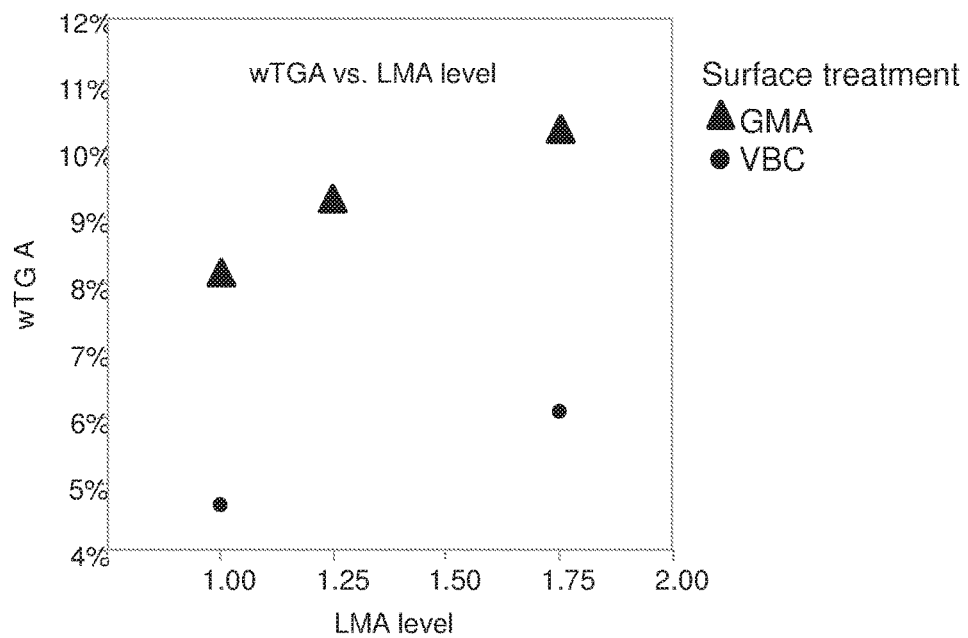
FIG. 5 shows washed thermogravimetric analysis (wTGA) values as a function of lauryl methacrylate (LMA) content for magenta pigments functionalized with glycidyl methacrylate (GMA) and 4-vinylbenzylchloride (VBC).
Figure 6:
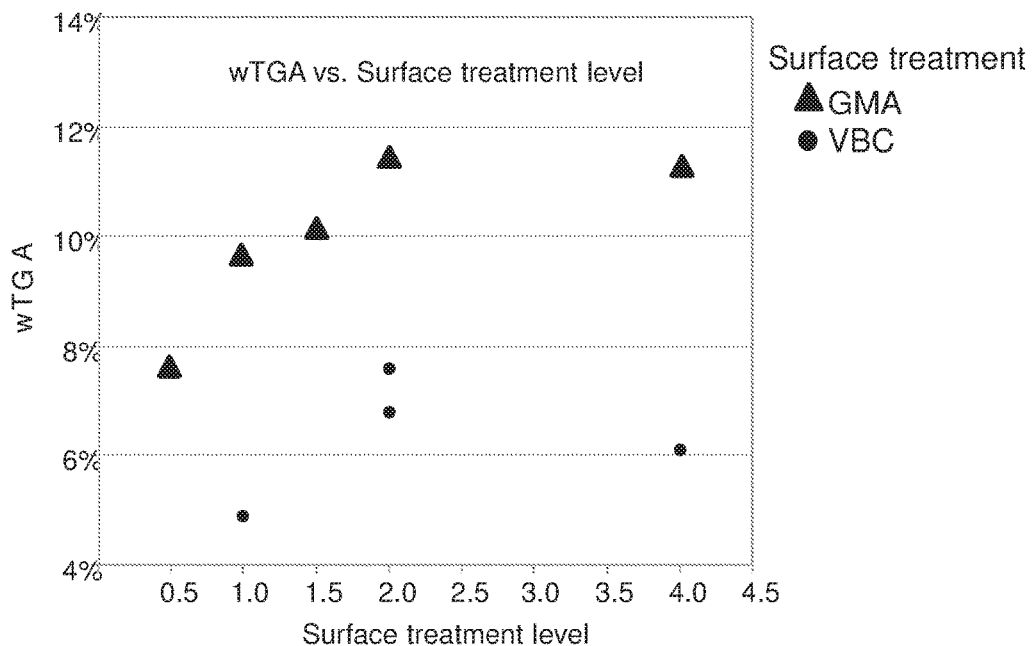
FIG. 6 shows washed thermogravimetric analysis (wTGA) values as a function of the amount of functionalization with glycidyl methacrylate (GMA) or 4-vinylbenzylchloride (VBC). The lauryl methacrylate content was constant at approximately 1.3 times the weight of the pigment.

FIG. 5 shows that pigments functionalized with GMA, in general, have a higher wTGA than similar pigments functionalized with VBC, when the level of LMA added during the coating step is identical. This result is likely due to improved grafting of LMA polymer with the GMA-functionalized pigments. As discussed above, the improved wTGA levels for GMA functionalized pigments will correlated with improved functionality in electrophoretic displays because of the higher organic content. It is also notable that increasing stoichiometric quantities of GMA result in higher organic content, as evidenced by FIG. 6 and the blue starred point in FIG. 5 corresponding to 2×GMA_1.75×LMA in Table 1. An additional benefit of using GMA instead of VBC is that GMA has a higher reactivity toward quinacridone pigments than VBC, thus the functionalization reaction can be completed in 2-4 hr at 45° C. versus overnight at 42° C. for VBC. See U.S. Patent Application No. 2014/0340430.

Example 2—Maleic Anhydride Functionalized Pigments

Part A: Preparation of a Magenta Pigment Dispersion

Ink Jet Magenta E 02 VP2621, available from Clariant, Basel, Switzerland, was dispersed in toluene. The resultant dispersion was transferred to a 500 mL round-bottomed flask and the flask degassed with nitrogen. The reaction mixture was then brought to 45° C., and, upon temperature equilibration, maleic anhydride was added and the reaction was allowed to stir at 65° C. for sixteen hours. The resulting reaction mixture was allowed to cool to room temperature and then poured into a 1 L plastic centrifuge bottle, diluted with toluene and centrifuged at 3500 RPM for 20 minutes. The centrifuge cake was washed twice with toluene, each time the mixture was centrifuged at 3500 RPM for 20 minutes. After the final wash, the supernatant was decanted and the resultant pigment was dried in a 70° C. vacuum oven overnight, then ground with a mortar and pestle. This procedure produces magenta pigment functionalized with an acrylate group to which a polymeric chain could be attached. See Formula IV.

The dried functionalized pigment thus was dispersed in toluene and laurel methacrylate (LMA) monomer with ball milling with Zirconox grinding media and a roll mill, and the resultant dispersion transferred to a jacketed 500 mL rector equipped with an overhead stirrer and brought to 65° C. via a circulating water bath. The system was purged with nitrogen for at least one hour, and then a solution of AIBN (2,2'-azobis(2-methylpropionitrile)) in toluene was metered into the reaction. The reaction mixture was stirred vigorously at 65° C. for 16 hours, then poured into a 1 L plastic centrifuge bottle, diluted with toluene and centrifuged at 4500 RPM for 30 minutes. The centrifuge cake was washed once with toluene and the mixture was again centrifuged at 4500 RPM for 30 minutes. The supernatant was decanted and the resultant pigment was dried in a 70° C. vacuum oven overnight. This procedure produces a magenta pigment with a covalently bound polymeric shell with a typical molecular weight of 35-120 kDA. See Formula V. The polymerized pigment was then ground with a mortar and pestle, and dispersed in ISOPAR® E to form a 20 weight % dispersion, which was sonicated and rolled on a roll mill for 24 hours. The resultant dispersion was filtered through fabric mesh to remove any large particles, a sample removed and its solids content measured.

Example 3 (Prophetic)—4-Methacryloxyethyl Trimellitic Anhydride Functionalized Pigments Part A: Preparation of a Magenta Pigment Dispersion Ink Jet Magenta E 02 VP2621, available from Clariant, Basel, Switzerland, will be dispersed in toluene. The resultant dispersion will be transferred to a 500 mL round-bottomed flask and the flask degassed with nitrogen. The reaction mixture will then be brought to 45° C., and, upon temperature equilibration, 4-methacryloxyethyl trimellitic anhydride will be added and the reaction was allowed to stir at 65° C. for sixteen hours. The resulting reaction mixture will be allowed to cool to room temperature and then poured into a 1 L plastic centrifuge bottle, diluted with toluene and centrifuged at 3500 RPM for 20 minutes. The centrifuge cake will be washed twice with toluene, each time the mixture will be centrifuged at 3500 RPM for 20 minutes. After the final wash, the supernatant will be decanted and the resultant pigment will be dried in a 70° C. vacuum oven overnight, then ground with a mortar and pestle. This procedure will produce magenta pigment functionalized with an acrylate group to which a polymeric chain could be attached.

The dried functionalized pigment will be dispersed in toluene and lauryl methacrylate (LMA) monomer with ball milling with Zirconox grinding media and a roll mill, and the resultant dispersion will be transferred to a jacketed 500 mL rector equipped with an overhead stirrer and brought to 65° C. via a circulating water bath. The system will be purged with nitrogen for at least one hour, and then a solution of AIBN (2,2'-azobis(2-methylpropionitrile)) in toluene will be metered into the reaction. The reaction mixture will be stirred vigorously at 65° C. for 16 hours, then poured into a 1 L plastic centrifuge bottle, diluted with toluene and centrifuged at 4500 RPM for 30 minutes. The centrifuge cake will be washed once with toluene and the mixture will be again centrifuged at 4500 RPM for 30 minutes. The supernatant will be decanted and the resultant pigment will be dried in a 70° C. vacuum oven overnight. This procedure will produce a magenta pigment with a covalently bound polymeric shell with a typical molecular weight of 35-120 kDA. The polymerized pigment will be ground with a mortar and pestle, and dispersed in ISOPAR® E to form a 20 weight % dispersion, which will be sonicated and rolled on a roll mill for 24 hours. The resultant dispersion will be filtered through fabric mesh to remove any large particles, a sample will be removed and its solids content will be measured.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

The invention claimed is:

1. A pigment comprising Formula VI:

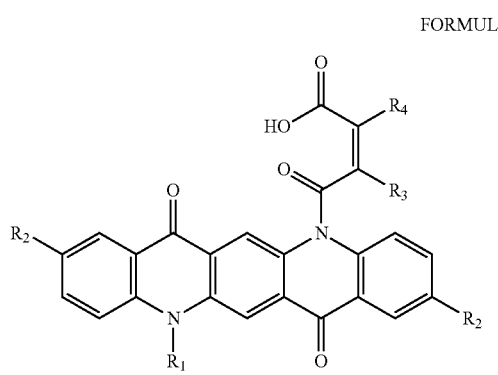

FORMULA VI wherein $R_1$ is a hydrogen, a $C_1$-$C_3$ alkyl group, a halogen, a hydroxyl, or —$COCR_3CR_4COOH$;

$R_2$ is a hydrogen, $C_1$-$C_3$ alkyl group, or a halogen;

$R_3$ is hydrogen or a hydrophobic polymer having a molecular weight between 5 kD and 100 kD; and $R_4$ is hydrogen or a hydrophobic polymer having a molecular weight between 5 kD and 100 kD.

2. The pigment of claim 1, wherein the hydrophobic polymer is a polymer comprising lauryl acrylate, lauryl methacrylate, 2-ethylhexyl acrylate, 2-ethylhexyl methacrylate, hexyl acrylate, hexyl methacrylate, n-octyl acrylate, n-octyl methacrylate, n-octadecyl acrylate, n-octadecyl methacrylate, or a combination thereof.

3. The pigment of claim 1, comprising Formula VII:

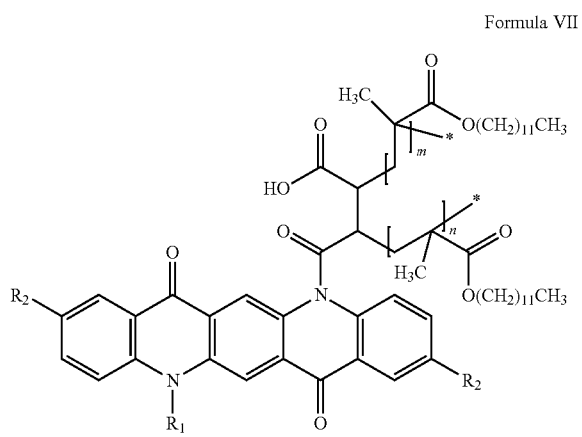

Formula VII wherein m and n are independently integers between 10 and 200.

4. The pigment of claim 1, comprising Formula VIII:

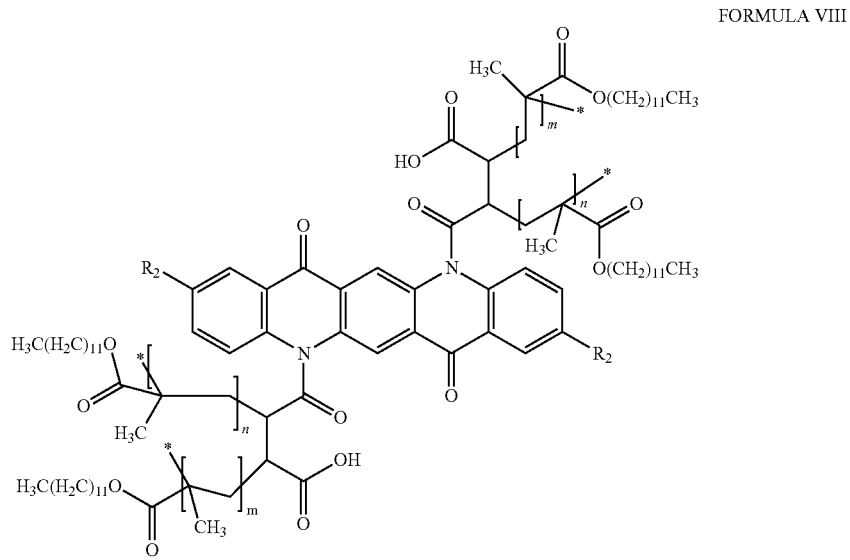

FORMULA VIII wherein m and n are independently integers between 10 and 200.

5. The pigment of claim 1, wherein $R_2$ is —H or $R_2$ is —$CH_3$.

6. An electrophoretic a medium comprising a pigment of claim 1.

7. An electro-optic display comprising a pigment of claim 1.

8. A front plane laminate comprising a pigment of claim 1.

* * * * *